(12) United States Patent
Goetz et al.

(10) Patent No.: US 10,471,272 B2
(45) Date of Patent: Nov. 12, 2019

(54) MAGNETIC NEUROSTIMULATION WITH REDUCED ACOUSTIC EMISSION

(71) Applicant: Stefan M. Goetz, Durham, NC (US)

(72) Inventors: Stefan M. Goetz, Durham, NC (US); David L. K. Murphy, Durham, NC (US); Angel V. Peterchev, Durham, NC (US)

( * ) Notice: Subject to any disclaimer, the term of this patent is extended or adjusted under 35 U.S.C. 154(b) by 86 days.

(21) Appl. No.: 14/745,419

(22) Filed: Jun. 20, 2015

(65) Prior Publication Data

US 2015/0367141 A1  Dec. 24, 2015

(30) Foreign Application Priority Data

Jun. 20, 2014  (GB) .................................. 1410987.0

(51) Int. Cl.
*A61N 2/02* (2006.01)
*A61N 2/00* (2006.01)
(Continued)

(52) U.S. Cl.
CPC ............... *A61N 2/02* (2013.01); *A61N 2/006* (2013.01); *H01F 27/022* (2013.01);
(Continued)

(58) Field of Classification Search
CPC ...... A61N 2/006; A61N 2/02; A61N 1/36071; A61N 1/40; A61N 2/008
See application file for complete search history.

(56) References Cited

U.S. PATENT DOCUMENTS 5,661,399 A  8/1997 Sellers et al.
6,075,363 A  6/2000 Sellers et al.
(Continued)

FOREIGN PATENT DOCUMENTS

EP  1042032 B1  6/2004
EP  2432547 B1  11/2014
(Continued)

OTHER PUBLICATIONS

Nikouline V. et al., "The role of the coil click in TMS assessed with simultaneous EEG", *Clinical Neurophysiology*, 1999, 110(8): pp. 1325-1328.
(Continued)

*Primary Examiner* — Christine H Matthews
(74) *Attorney, Agent, or Firm* — Kilpatrick Townsend & Stockton LLP

(57) ABSTRACT

The invention relates to a device and a method for the stimulation of neurons and muscle cells according to the principle of magnetic stimulation, wherein the invention generates substantially less acoustic sound emission for the same activation strength compared to the state of the art. This invention reduces the acoustic sound emission, usually a clicking sound, which is a safety risk in magnetic stimulation and causes undesired uncontrollable sensory-auditory brain stimulation, by increasing the frequency of a substantial portion of the spectrum of the pulse, preferably to or above the human hearing range.

Furthermore, the invention relates to a quiet coil technology that reduces the conversion of electrical energy into mechanic-acoustic oscillations, whereby the transmission of the mechanic-acoustic oscillations to the surface is suppressed by elastic decoupling and the mechanic-acoustic energy is converted into heat by viscoelastic material deformation instead.

15 Claims, 15 Drawing Sheets

(51) Int. Cl.
  H01F 27/28    (2006.01)
  H01F 27/02    (2006.01)
  H01F 27/32    (2006.01)
(52) U.S. Cl.
  CPC ..... *H01F 27/2823* (2013.01); *H01F 27/2871* (2013.01); *H01F 27/323* (2013.01)

(56) References Cited

U.S. PATENT DOCUMENTS

| | | | |
|---|---|---|---|
| 2001/0031906 A1* | 10/2001 | Ishikawa | A61N 2/008 |
| | | | 600/13 |
| 2003/0065322 A1* | 4/2003 | Panescu | A61B 5/0422 |
| | | | 606/41 |
| 2003/0158583 A1* | 8/2003 | Burnett | A61N 1/36071 |
| | | | 607/2 |
| 2004/0251901 A1 | 12/2004 | Tsuda et al. | |
| 2012/0108883 A1 | 5/2012 | Peterchev | |
| 2013/0043870 A1 | 2/2013 | De Lima et al. | |
| 2013/0048415 A1 | 2/2013 | De Lima | |
| 2015/0190648 A1 | 7/2015 | Fischell et al. | |

FOREIGN PATENT DOCUMENTS

| | | |
|---|---|---|
| GB | 1410987 | 10/1975 |
| WO | 9927995 A1 | 6/1999 |
| WO | 2006/124914 A2 | 11/2006 |
| WO | 2013/165470 A1 | 11/2013 |

OTHER PUBLICATIONS

Counter S.A. et al., "Analysis of the coil generated impulse noise in extracranial magnetic stimulation", *Electroencephalography and Clinical Neurophysiology*, 1992, 85(4):pp. 280-288.

Counter S.A., et al., "Acoustic trauma in extracranial magnetic brain stimulation", *Electroencephalography and Clinical Neurophysiology*, 1991, 78(3): pp. 173-184.

Rossi S., et al., "Safety, ethical considerations, and application guidelines for the use of transcranial magnetic stimulation in clinical practice and research", *Clinical Neurophysiology*, 2009,120(12): pp. 2008-2039.

Zangen, A., et al., "Transcranial magnetic stimulation of deep brain regions: evidence for efficacy of the H-coil", *Clinical Neurophysiology*, 2005, 116(4): pp. 775-779.

Baguley, D.M., "Hyperacusis", *Journal of the Royal Society of Medicine*, 2003, 96(12): pp. 582-585.

Coelho C.B., et al., "Hyperacusis, sound annoyance, and loudness hypersensitivity in children", *Progress in brain research*, 2007, 166: pp. 169-178.

Loo C.K., et al., "A review of the safety of repetitive transcranial magnetic stimulation as a clinical treatment for depression", *International Journal of Neuropsychopharmacology*, 2008, 11(1): pp. 131-147.

Machii K., et al., "Safety of rTMS to non-motor cortical areas in healthy participants and patients", *Clinical Neurophysiology*, 2006, 117(2): pp. 455-471.

Janicak P.G., et al., "Transcranial magnetic stimulation in the treatment of major depressive disorder: A comprehensive summary of safety experience from acute exposure, extended exposure, and during reintroduction treatment", *Journal of Clinical Psychiatry*, 2008, 69(2): pp. 222-232.

Martin P.R., et al., "Noise as a trigger for headaches: Relationship between exposure and Sensitivity", *Headache*, 2006, 46(6): pp. 962-972.

Wober C. et al., "Triggers of migraine and tension-type headache. Handbook of Clinical", *Neurology*, 2010, 97: pp. 161-172.

Komssi S., et al., he novelty value of the combined use of electroencephalography and transcranial magnetic stimulation for neuroscience research. Brain Research Reviews, 2006, 52(1): pp. 183-192.

Clapp W.C., et al., "Induction of LTP in the human auditory cortex by sensory stimulation", *European Journal of Neuroscience*, 2005, 22(5): pp. 1135-1140.

Clapp W.C., et al., "Translating Long-Term Potentiation from Animals to Humans: A Novel Method for Noninvasive Assessment of Cortical Plasticity", *Biological Psychiatry*, 2012, 71(6): pp. 496-502.

Zaehle T., et al., "Induction of LTP-like changes in human auditory cortex by rapid auditory stimulation: An FMRI study", *Restorative Neurology and Neuroscience*, 2007, 25(3-4): pp. 251-259.

TAL (1998), German Technical Instruction on Noise Protection According to the Federal Control of Pollution Act BlmchG/ Technische Anleitung zum Schutz gegen Larm erlassen auf der Basis des Bundesimmissionsschutzgesetzes. GMBI No. 26/1998, p. 503.

Rampilainen, et al, "The noise level in magnetic stimulation", *Scandinavian Audiology*, 1996, 25(4): pp. 223-226.

Duck F.A., "Medical and non-medical protection standards for ultrsound and infrasound", *Progress in Biophysics and Molecular Biology*, 2007, 93(1-3): pp. 176-191.

Barker A.T. et al., "Magnetic nerve stimulation: the effect of waveform on efficiency, determination ofneural membrane time constants and the measurement of stimulator output", *Electroencephalography 300 and clinical neurophysiology*, 1991, Supplement 43: pp. 227-237.

Goetz S.M., et al., "Analysis and Optimization of Pulse Dynamics for MagneticStimulation". *PLOS One*, 2013, 8(3): e55771.

Peterchev A.V., et al., "A transcranial magnetic stimulator inducing nearrectangular pulses with controllable pulse width (cTMS)", *IEEE Transactions on Biomedical Engineering*, 2008, 55(1): pp. 257-266.

Peterchev A.V., et al., "Repetitive transcranial magnetic stimulator with controllable pulse parameters", *Journal of Neural Engineering*, 2011, 8:036016.

Peterchev, A.V., et al., "Advances in Transcranial Magnetic Stimulation Technology", Department of Psychiatry and Behavioral Sciences, Duke University School of Medicine, Durham, NC, USa, Reti. C10.txs, 2014, pp. 186.

Goetz S.M., et al., "Circuit topology and control principle for a first magnetic stimulator with fully controllable waveform", *Proceedings of the IEEE Engineering in Medicine and Biology Society (EMBC)*, 2012, 4700-4703, doi:l0.1109/EMBC.2012.6347016.

Litvak E., et al., "Health and safety implications of exposure to electromagnetic fields in the frequency range 300 Hz to 10 MHz", *Bioelectromagnetics*, 2002, 23(1): pp. 68-82.

Goetz, et al., "The development and modelling of devices and paradigms for transcranial magnetic stimulation", *International Review of Psychiatry*, 2017, vol. 29 (2), pp. 115-145.

Emrich D., et al., "Muscle force development after low-frequency magnetic burst stimulation in dogs", *Muscle & nerve*, 2012, 46(6): pp. 951-959.

Wada S., Kubota H., Maita S., Yamamoto I., Yamaguchi M., Andoh T., Kawakami T., Okumura F., and Takenaka T. p. 13 of 31 (1996). Effects of stimulus waveform on magnetic nerve stimulation. Japanese Journal of Applied Physics, 35:1983-1988.

* cited by examiner

Equivalences

| | | | |
|---|---|---|---|
| Stiffness $E$ | $\frac{d}{dt}\langle p \rangle = k_1 E \langle v \rangle$ | $C\frac{d}{dt}V = I$ | Capacitance $C$ |
| Mass $m$ | $\langle p \rangle = Am\frac{d}{dt}\langle v \rangle$ | $V = L\frac{d}{dt}I$ | Inductance $L$ |
| Viscoelasticity/ Viscosity $\eta$ | $\langle p \rangle = k_2 \eta \langle v \rangle$ | $V = RI$ | Resistance $R$ |

Fig. 11

MAGNETIC NEUROSTIMULATION WITH REDUCED ACOUSTIC EMISSION

BACKGROUND

This applications claims priority of United Kingdom Patent Application GB 14 10987.0, filed Jun. 20, 2014.

The invention relates to a device and a method for the stimulation of neurons and muscle cells according to the principle of magnetic stimulation, while the invention generates substantially less acoustic sound emission for the same activation strength compared to the state of the art. This invention reduces the acoustic sound emission, usually a clicking sound, which is a safety risk in magnetic stimulation and causes undesired uncontrollable sensory-auditory brain stimulation, by increasing the frequency of a substantial portion of the spectrum of the pulse, preferably to or above the human hearing range. Furthermore, the invention relates to a quiet coil technology that reduces the conversion of electrical energy into mechanic-acoustic oscillations, whereby the transmission of the mechanic-acoustic oscillations to the surface is suppressed by elastic decoupling and the mechanic-acoustic energy is converted into heat by viscoelastic material deformation instead.

Transcranial magnetic stimulation (TMS) is a technique for non-invasive brain stimulation with strong, brief magnetic pulses that induce an electric field in the brain. TMS is widely used in the neurosciences as a tool for probing brain function. It is also an FDA-approved treatment for depression, and is under study for other psychiatric and neurological disorders. TMS has been demonstrated to enhance cognitive function in healthy subjects as well.

A TMS device includes a pulse generator and a stimulation coil that is placed on the subject's head.

Typical TMS devices generate coil current pulses that are sinusoidal with main frequency component of 1-5 kHz, current amplitude up to 8 kA, and resulting magnetic field strength on the coil surfaces up to 2.5 T. The high amplitude pulses result in electromagnetic mechanical forces within the pulse generator, the stimulation coil, and the cable connecting them. Of these, the sound of the TMS coil is dominant due to the strong magnetic field in the coil and is most difficult to suppress since the coil is placed on the subject's head, where it is conducted by air and skull bone [Nikouline V., Ruohonen J., and Ilmoniemi R. J. (1999). The role of the coil click in TMS assessed with simultaneous EEG. Clinical Neurophysiology, 110(8):1325-1328.]. The mechanical vibration produced by the forces results, in turn, in a loud click sound that may be as high as 120-140 dB 10 cm from the coil, and have peak spectral power in the 1-7 kHz range [Starck J., Rimpilainen I., Pyykko I, and Toppila E. (1996). The noise level in magnetic stimulation. Scandinavian Audiology, 25(4): 223-226; Counter S. A., Borg E. (1992) Analysis of the coil generated impulse noise in extracranial magnetic stimulation. Electroencephalography and Clinical Neurophysiology, 85(4):280-288.]. The loud noise generated by conventional devices is a significant limitation of TMS, having the following key disadvantages:

(1) The loud click noise can cause hearing damage in the TMS subject, TMS operator, and other persons or experimental animals in the vicinity of the system [Counter S. A., Borg E. (1992) Analysis of the coil generated impulse noise in extracranial magnetic stimulation. Electroencephalography and Clinical Neurophysiology, 85(4):280-288; Counter S. A., Borg E., and Lofqvist L. (1991). Acoustic trauma in extracranial magnetic brain stimulation. Electroencephalography and Clinical Neurophysiology, 78(3):173-184; Rossi S., Hallett M., Rossini P. M., and Pascual-Leone A. (2009). Safety, ethical considerations, and application guidelines for the use of transcranial magnetic stimulation in clinical practice and research. Clinical Neurophysiology, 120(12): 2008-2039.]. Therefore, anyone in the immediate vicinity of the TMS device is required to wear hearing protection, for example ear plugs or earphones [Rossi S., Hallett M., Rossini P. M., and Pascual-Leone A. (2009). Safety, ethical considerations, and application guidelines for the use of transcranial magnetic stimulation in clinical practice and research. Clinical Neurophysiology, 120(12):2008-2039.]. Failure of the hearing protection can expose to risk of hearing loss, as exemplified by the occurrence of permanent hearing loss in a subject whose ear protection had fallen out during an rTMS session [Zangen, A., Y. Roth, et al. (2005). Transcranial magnetic stimulation of deep brain regions: evidence for efficacy of the H-coil. Clinical Neurophysiology, 116(4):775-779.]. The risk of impact on hearing may be higher in children [Rossi S., Hallett M., Rossini P. M., and Pascual-Leone A. (2009). Safety, ethical considerations, and application guidelines for the use of transcranial magnetic stimulation in clinical practice and research. Clinical Neurophysiology, 120(12):2008-2039.]. This issue is exacerbated in environments where the mechanical forces are increased and/or acoustic reverberation is present, for example in magnetic resonance imaging (MRI) scanners during interleaved TMS and functional MRI (fMRI).

(2) Even with hearing protection, the auditory perception of the TMS sound is substantial and often unpleasant or intolerable to the subject or patient receiving TMS, the TMS operator, or other persons in the vicinity of the TMS device. Intolerance may be particularly pronounced for persons with increased sensitivity to noise (hyperacusis). Hyperacusis is estimated to affect 8-15% of the general population [Baguley, D. M. (2003). Hyperacusis. Journal of the Royal Society of Medicine, 96(12): 582-585; Coelho C. B., Sanchez T. G., and Tyler R. S. (2007). Hyperacusis, sound annoyance, and loudness hypersensitivity in children. Progress in brain research 166:169-178.] and has a higher prevalence in patients with some psychiatric and neurological disorders, including tinnitus, migraine, autism spectrum disorder, depression, and post-traumatic stress disorder as well as other anxiety disorders. For these disorders, TMS is either approved (depression) or investigated as a therapeutic intervention. Furthermore, tension-type headache is the most common side effect of rTMS, occurring in 23%-58% of subjects or patients and in 16%-55% of those receiving sham [Loo C. K., McFarcluhar T. F., and Mitchell P. B. (2008). A review of the safety of repetitive transcranial magnetic stimulation as a clinical treatment for depression. International Journal of Neuropsychopharmacology, 11(1):131-147; Machii K., Cohen D., Ramos-Estebanez C., and Pascual-Leone A. (2006). Safety of rTMS to non-motor cortical areas in healthy participants and patients. Clinical Neurophysiology, 117(2):455-471; Janicak P. G., O'Reardon J. P., Sampson S. M., Husain M. M., Lisanby S. H., Rado T. J., Heart K. L., and Demitrack M. A. (2008). Transcranial magnetic stimulation in the treatment of major depressive disorder: A comprehensive summary of safety experience from acute exposure, extended exposure, and during reintroduction treatment. Journal of Clinical Psychiatry, 69(2): 222-232.]. Since tension-type headache can be triggered by exposure to noise [Martin P. R., Reece J., and Forsyth M. (2006). Noise as a trigger for headaches: Relationship between exposure and sensitivity. Headache, 46(6):962-972; Wober C. and Wober-Bingol C. (2010). Triggers of migraine and tension-type headache. Handbook of Clinical Neurology, 97:161-172.] it is a distinct possibility that the noise generated by the TMS device is a contributor. Scalp nerve and muscle stimulation and scalp pressure from the coil and other hardware during TMS likely contribute to headache as well (Borckardt et al., 2010; Trevino et al., 2011). However, sham TMS typically reproduces the coil sound but not the scalp stimulation (Maizey et al., 2013). Therefore, the occurrence of headache in sham TMS, in some cases at similar rates as in active TMS (Janicak et al., 2008; Maizey et al., 2013), supports a role of the TMS device noise as a headache trigger. Therefore, in some patient groups, the TMS device noise may present an obstacle to receiving potentially beneficial treatment.

(3) The auditory perception of the TMS sound results in an evoked response in the brain that is not generated by the magnetic stimulus, but is nevertheless synchronous with it. Thus, it is difficult to decouple the effect of the magnetic pulse from the auditory response [Komssi S., and Kahkonen S. (2006). The novelty value of the combined use of electroencephalography and transcranial magnetic stimulation for neuroscience research. Brain Research Reviews, 52(1): 183-192.]. This can confound experimental studies and can produce unintended modulation and interaction effects in clinical applications. Repetitive auditory stimulation, for instance, can also induce long term potentiation (LTP) in the brain [Clapp W. C., Kirk I. J., Hamm J. P., Shepherd D., and Teyler T. J. (2005). Induction of LTP in the human auditory cortex by sensory stimulation. European Journal of Neuroscience, 22(5):1135-1140; Clapp W. C., Hamm J. P., Kirk I. J., and Teyler T. J. (2012). Translating Long-Term Potentiation from Animals to Humans: A Novel Method for Noninvasive Assessment of Cortical Plasticity. Biological Psychiatry, 71(6):496-502; Zaehle T., Clapp W. C., Hamm J. P., Meyer M., and Kirk I. J. (2007). Induction of LTP-like changes in human auditory cortex by rapid auditory stimulation: An FMRI study. Restorative Neurology and Neuroscience, 25 (3-4):251-259.], which overlays the modulation effect in rTMS. For example, one of the FDA-approved rTMS depression paradigms uses 10 Hz pulse trains, which corresponds to the frequency range of highest auditory cortex sensitivity (10-14 Hz) and is close to the frequency at which auditory-induced LTP has been demonstrated in humans (13 Hz, see [Clapp W. C., Hamm J. P., Kirk I. J., and Teyler T. J. (2012). Translating Long-Term Potentiation from Animals to Humans: A Novel Method for Noninvasive Assessment of Cortical Plasticity. Biological Psychiatry, 71(6):496-502.]

(4) The loud noise generated by TMS devices presents challenges to the environment where the TMS device is located and operated. Since the sound of the TMS device may penetrate neighboring rooms in the building, researchers and physicians using TMS devices face challenges from other occupants and/or the management of the building where the device is located. Moreover, in many countries, noise emission is restricted by regulations. Since many medical offices are not located in designated industrial areas, emission limits as strict as 55 dB(A) outside and 35 dB(A) in neighboring units within the building can apply [TAL (1998), German Technical Instruction on Noise Protection According to the Federal Control of Pollution Act BlmSchG/ Technische Anleitung zum Schutz gegen Lärm erlassen auf der Basis des Bundesimmissionsschutzgesetzes. GMBI No. 26/1998, p. 503.]. Without enhanced noise abatement measures in the building, the use of TMS for medical purposes may be restricted.

Many of these considerations apply to devices for peripheral magnetic stimulation as well. Therefore, the principles of this invention are applicable to peripheral magnetic stimulation devices as well.

State-of-the-Art Approaches to Low Noise TMS

To reduce the noise generated by the TMS device, some manufacturers use techniques to dampen oscillations in the stimulation coil. The effectiveness of this approach has been limited, as evidenced by the high noise level of commercially available devices [Starck J., Rimpilainen I., Pyykko I, and Toppila E. (1996). The noise level in magnetic stimulation. Scandinavian Audiology, 25(4): 223-226; Counter S. A., Borg E. (1992) Analysis of the coil generated impulse noise in extracranial magnetic stimulation. Electroencephalography and Clinical Neurophysiology, 85(4):280-288.]. A proposed approach for more drastic noise reduction involves placing the coil winding in an evacuated vessel [Ilmoniemi R. J. et al. (1997). EP 1042032, WO 99/27995]. That approach attempts to minimize the acoustic emission by omitting all media for sound transmission around the coil winding. This approach, however, has a number of shortcomings: (1) The air-tight, evacuated vessel around the coil could increase the spacing between the coil winding and the stimulation target thus worsening the electromagnetic coupling to the target and, hence, the electrical efficiency of the system. (2) There would be alternative noise conduction paths from the points where the coil conductor enters the evacuated vessel, from the coil cable, and from the pulse generator. (3) The evacuated vessel system would be large, inflexible, impractical, potentially fragile, and expensive.

Therefore, there is a compelling need for the development of TMS devices that generate less noise since existing or proposed TMS systems do not offer adequate solution to the problem. Addressing this need, the invention proposes the concept of a quiet TMS technology that could substantially reduce the noise generated by TMS.

Figure 1:
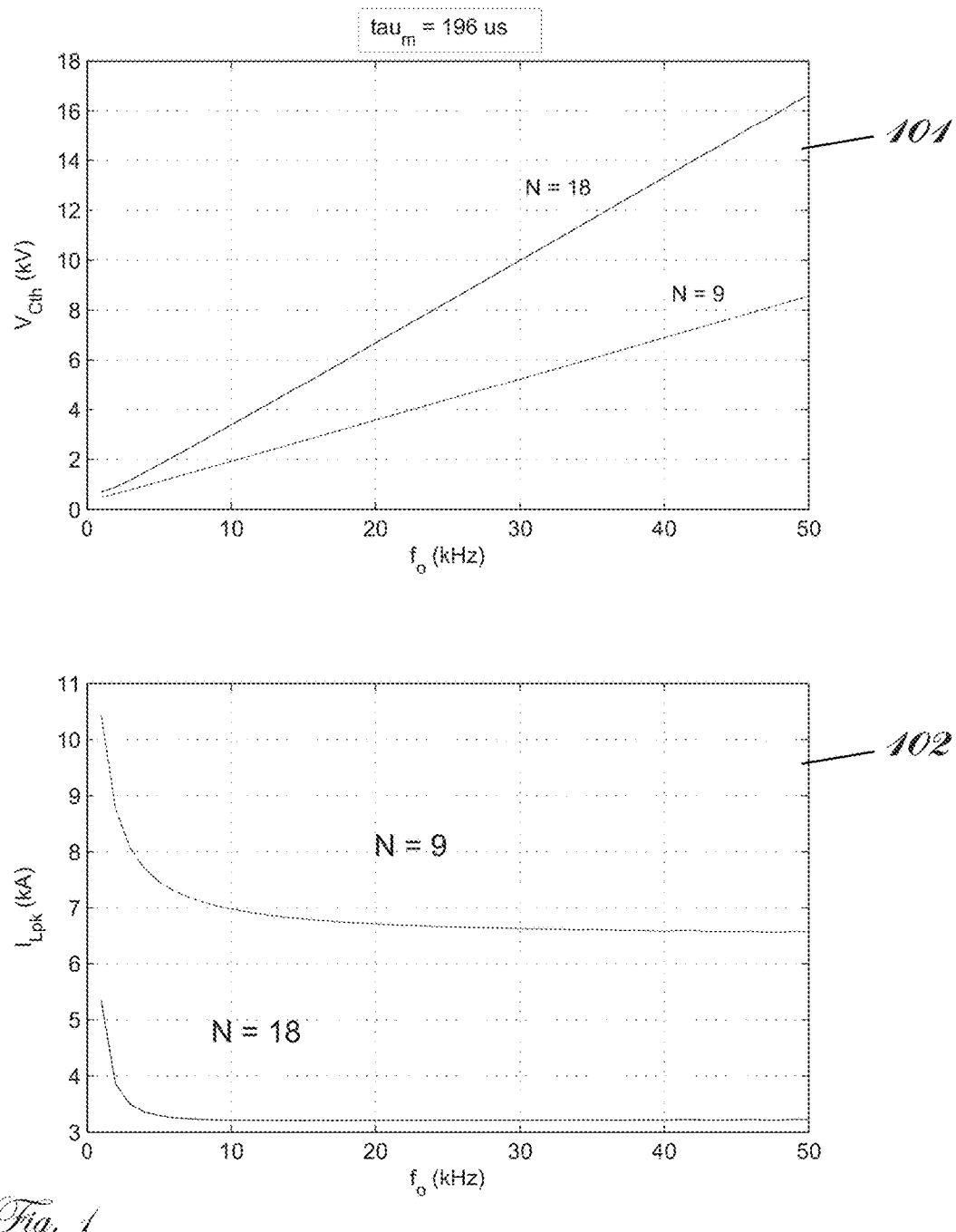
FIG. 1 shows the threshold capacitor voltage (101), $V_{Cth}$, and peak coil current (102), $I_{Lpk}$, at the approximate cortical activation threshold as a function of pulse frequency $f_0$ assuming first order neural membrane response with $\tau_m=196$ µs. This is based on the parameters of a Magstim figure-8 coil. The data for number of turns, N, of 18 (conventional Magstim figure-8) and for N=9 are plotted.

Conductor (501): preferably with high density, preferably stiff, preferably thick (avoidance of bending modes in transverse direction), preferably no inhomogeneous mass or mass density (dimilar thickness to avoid cantilever); stiff core (502); stiff connection (503): e.g., epoxy-kapton compound, fiber compound, glass wool, aramid-epoxy compound (in case of kapton or polyimides surface treatment for adherence promotion recommended), stiff epoxy, or cyanoacrylate-epoxy; highly viscoelastic layer (504): preferably high Young's modulus, preferably high viscosity, for stiffening and providing mechanical energy losses; highly elastic layer (505): for decoupling; casing (506): preferably stiff and massive, potentially beams for stiffening and softer tails for a controlled forming of modes.

Figure 5:
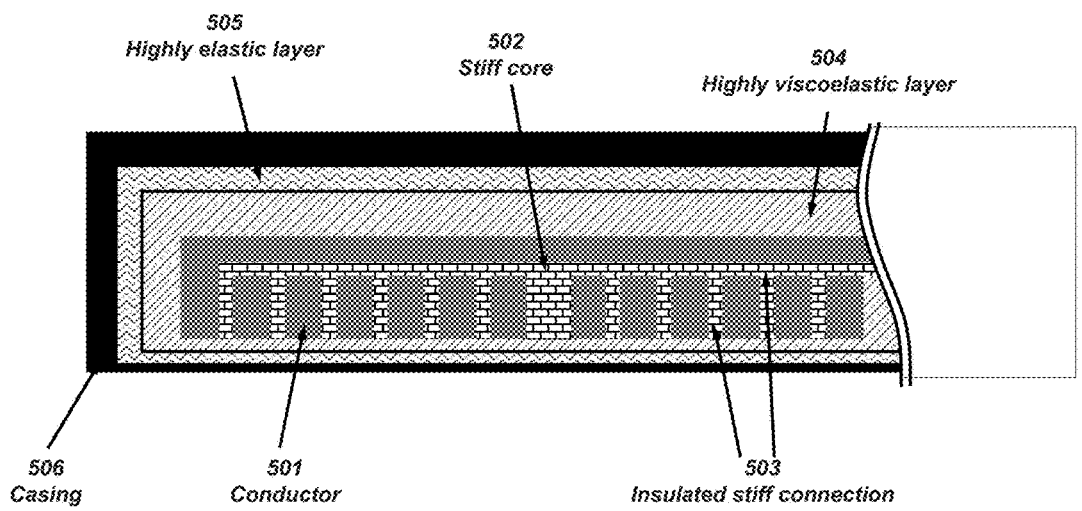
FIG. 5 shows a cross section of a coil according to the first embodiment of the mechanical part of the invention. The single turns of the conductor (501) are electrically insulated and tightly connected to each other. This connection (503) is implemented with a high stiffness (characterized by a high E-modulus). The connection between the outmost turn and the cable or a second loop, for instance, in a so-called figure-of-eight/butterfly coil can be used as a mechanically stabilizing beam as shown here. All gaps can furthermore be filled with stiff materials as indicated in the figure by the "stiff core" (502). This entire stiff block formed by the single conductors is decoupled from the casing and the environment by one layer of a viscoelastic material (504) (high $\eta$ value, additionally high E-modulus is advantageous) and another layer of a highly elastic material (505) (low E-modulus and Shore hardness). These layers may be repeated. Furthermore, the sequence may also end with a viscoelastic layer on both sides, i.e., as the inmost and outmost layer. A casing (506), preferably stiff and/or massive, closes the coil and forms the interface to the environment. Since one side of the coil is usually applied to a subject, the layer thicknesses may be different (e.g., smaller) than the others on this side. Likewise, the remaining sides do not need to have equal layer thicknesses.
Figure 6:
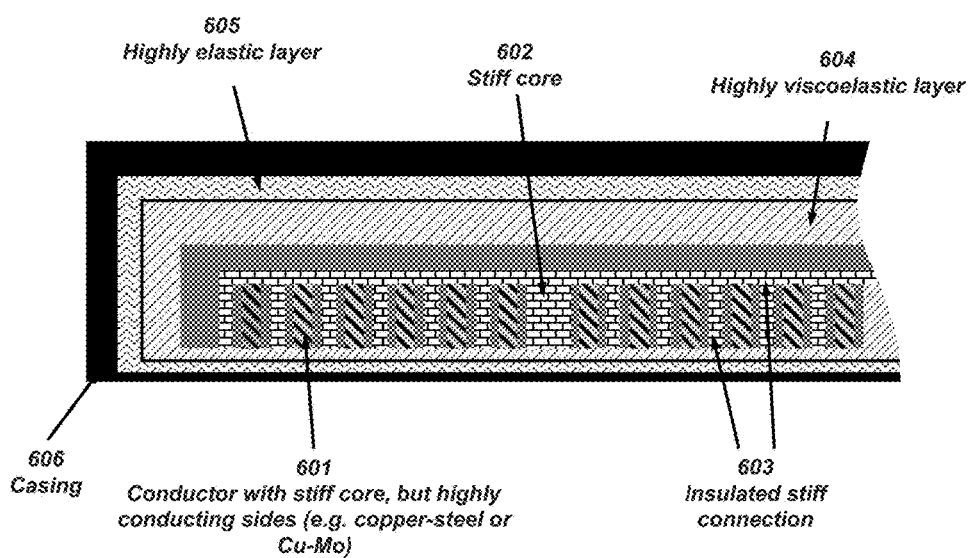

FIG. 6 shows a special embodiment in which the conductors of the implementation in FIG. 5 are copper-clad steel conductors (601). In this case, the conductor is shaped as a flat wire with a steel core that is covered by copper on both sides. Other wire shapes may be used instead.

Figure 7:
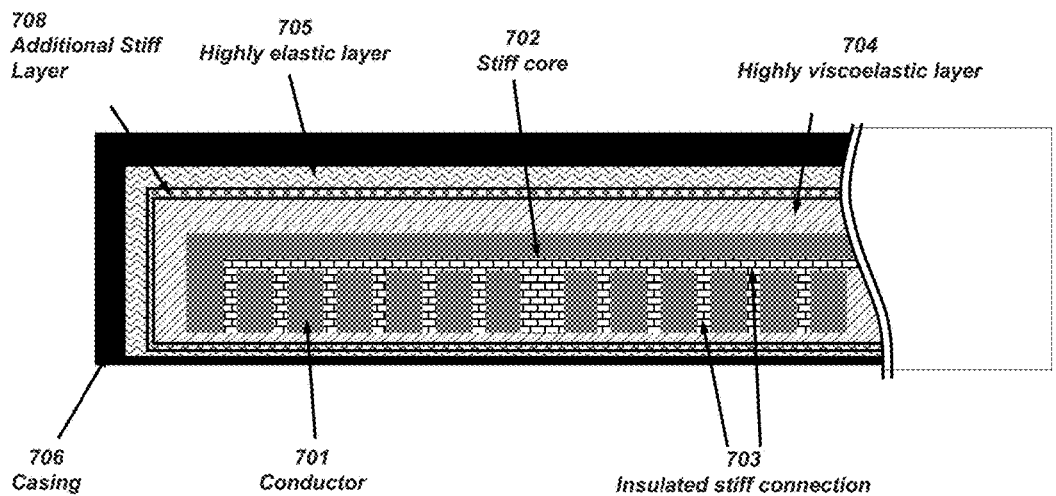

FIG. 7 shows a modification of the coil cross section in FIG. 5 in which the effect of the viscoelastic layer is enhanced by an additional stiff layer (708). In this case, the viscoelastic layer (704) is placed between two stiff layers (702, 708). This ensures that the oscillations always drive the viscous material properties of this layer and enforce shear stress, bending and compression; otherwise, oscillations could just displace the viscoelastic layer, which is relatively stiff, or excite modes with relatively low viscous energy loss. This layer does not have to be on all sides or form a closed surface; a stiff grid may be sufficient. An alternative to a stiff layer can also be stiff grains or beams in the viscoelastic layer that enforce bending of the viscoelastic material.

Figure 8:
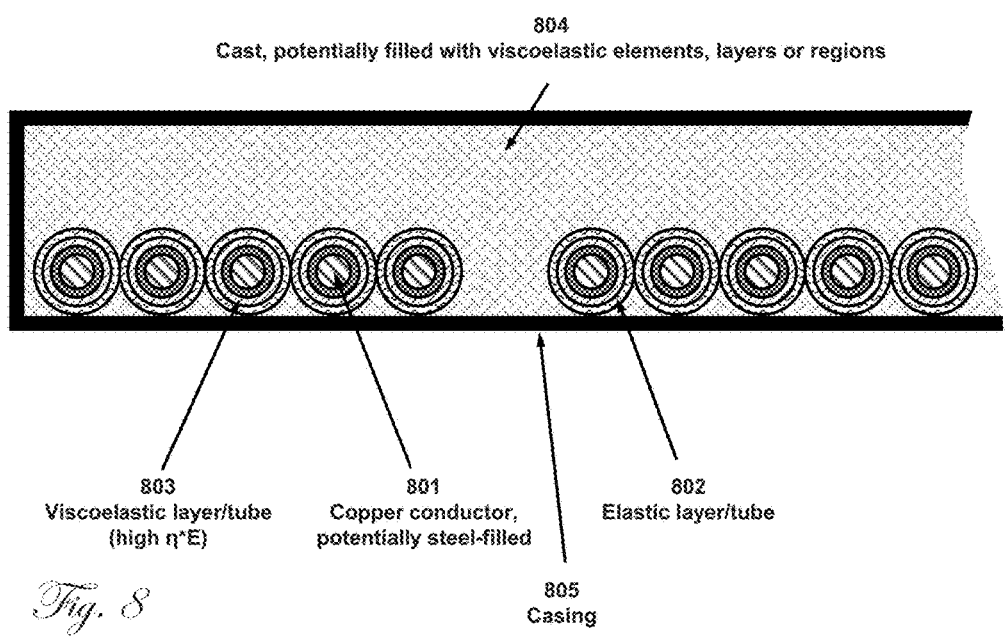

FIG. 8 shows a cross section of a coil according to the second embodiment of the mechanical part of the invention. The single turns (801) are treated individually in the same way as the larger block formed by several or all conductors or turns of the same conductor (801) in the first embodiment. The single turns are encompassed by individual viscoelastic layers (803) and individual elastic layers (802). In case of thick layers relative to the conductor spacing, the viscoelastic layers and/or the elastic layers of adjacent conductors or turns may touch each other and form a single layer. In case there is sufficient space, as shown here, the remaining gaps in the coil can be filled with a viscoelastic material (804). Alternatively, the material of the spatially closest layer can be used. For this embodiment, the casing encloses the coil and forms the interface to the environment. The conductors may be round or oval for a good surface-to-volume ratio. Furthermore, the conductor may be a copper-clad conductor, for example with a steel core.

Figure 9:
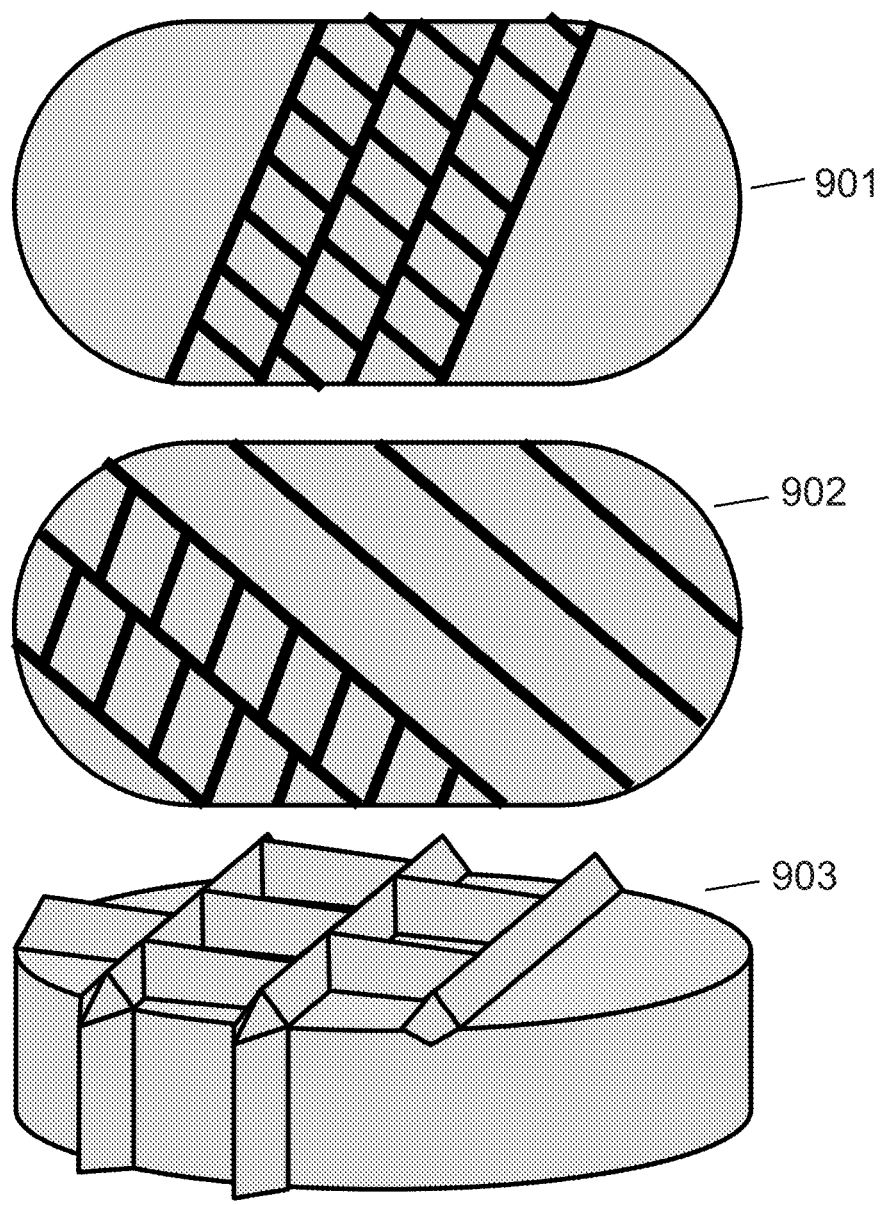

FIG. 9 shows the surface of a coil where several parts of the casing are additionally reinforced with known methods, e.g., with beams in order to increase the stiffness and/or the mass in general or for certain modes.

Figure 10:
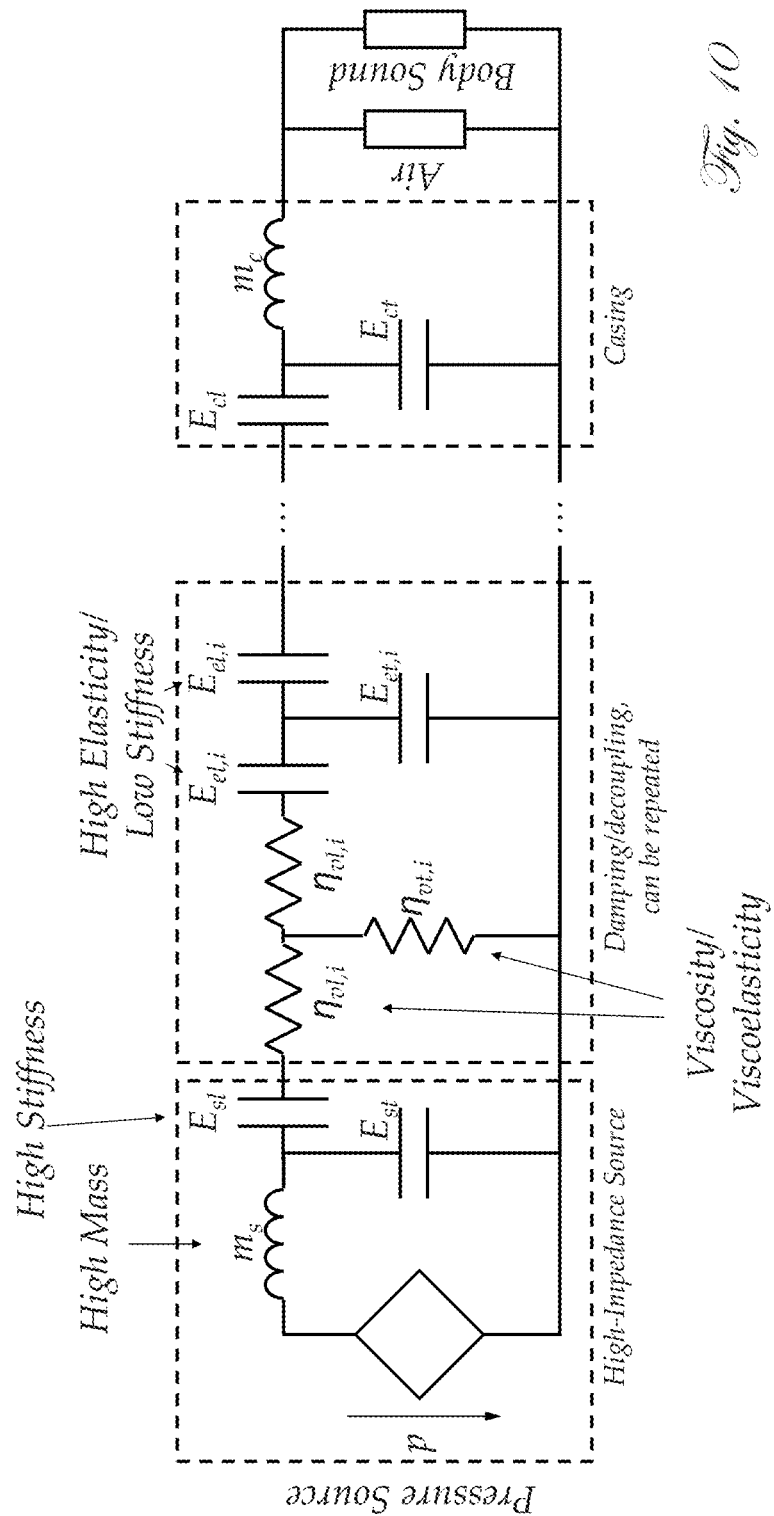

FIG. 10 shows a simplified equivalent-circuit model of the acoustic conditions of the second part of the invention and simplified equivalences with electrical components. A pressure source, i.e. a mechanical equivalent of an electrical voltage source, on the left side represents the conversion of electromagnetic energy to the acoustic domain. The high stiffness ($E_{st}$ and $E_{sl}$) and mass ($m_s$) of the conductor as favored by the invention increase the input impedance and minimize the amount of energy that is converted. Damping and decoupling units i, each formed by a viscoelastic layer (with viscosities $\eta_{vl,i}$ and $\eta_{vt,i}$) and an elastic layer (with E-moduli $E_{el,i}$ and $E_{et,i}$), convert the energy into heat and decouple their left side from their right side, respectively. These units can be repeated. The casing with mass $m_c$ and E-moduli $E_{cl}$ and $E_{ct}$ forms the interface to the environment to which it emits sound through the air and through body conduction. The electrical component equivalences are mostly a guideline since almost all known materials present strong frequency dependency of their parameters and strong nonlinearities. Furthermore, the description in terms of a one-dimensional circuit can only approximate the intricate three-dimensional geometric conditions.

FIG. 11 shows equivalences between electric and mechanic/acoustic phenomena.

Figure 12:
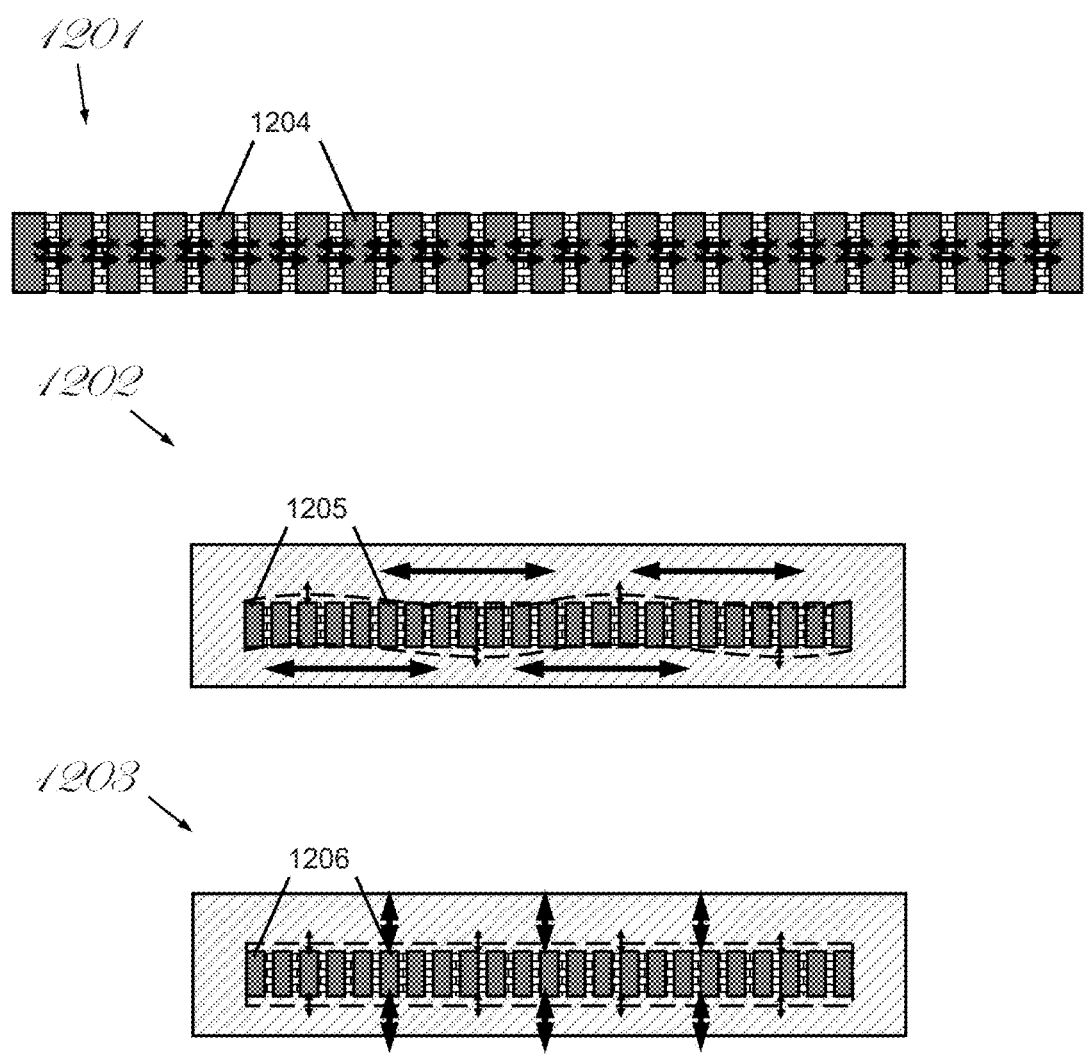

FIG. 12 illustrates the forces that cause the oscillations in a coil. Part 1201 shows the dominant direction of the forces between the conductor turns (1204, 1205, 1206) in a coil, which compress the material between the conductors or different turns of one conductor (1204, 1205, 1206). Part 1202 illustrates the conversion of bending modes in the core into shearing load in the viscoelastic layer. Part 1203 shows longitudinal oscillations (i.e., contraction and/or translation of the materials involved), which in TMS coils are more important for high frequency components, dependent on the specific material properties, mostly above the hearing limit.

Figure 13:
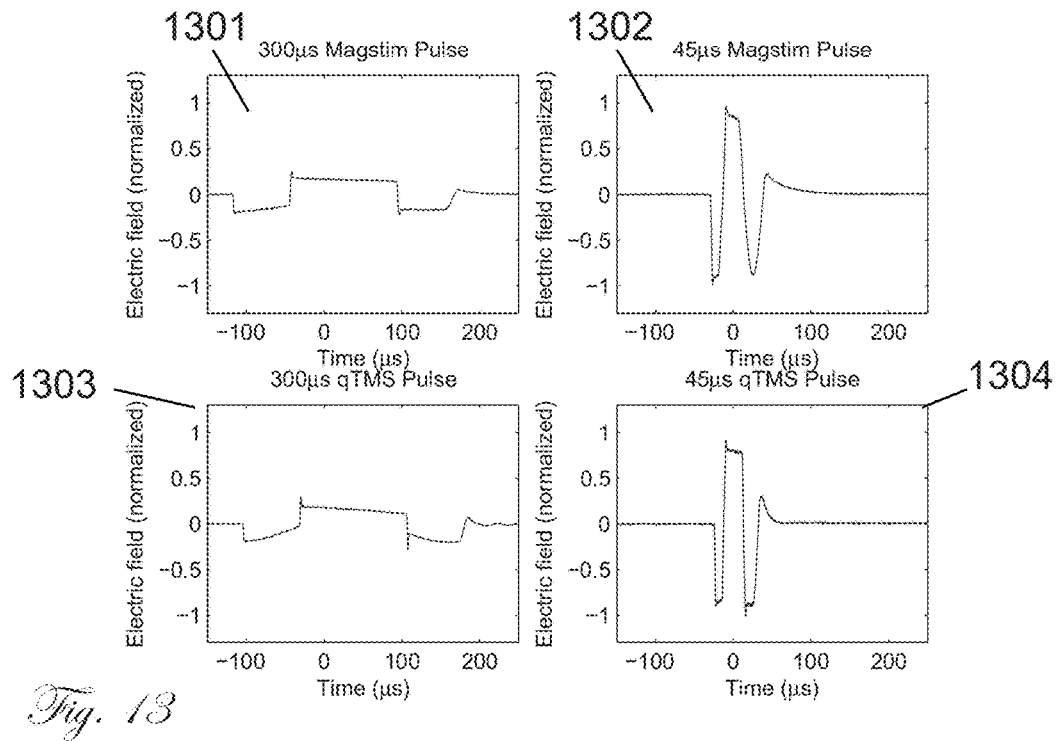

FIG. 13 shows the recorded waveforms of a TMS pulse of period 300 µs and a briefer 45 µs pulse. Both pulses are generated with a controllable pulse parameter TMS (cTMS)

device and a circular coil. The electric field generated by each pulse was measured with a single turn dI/dt probe. The peak neuronal depolarization induced by each pulse was modeled by passing the signal from the probe through a first order low-pass filter with a time-constant of 150 µs. The intensity of each pulse was set so that each pulse produced a peak-to-peak depolarization of 1000 mV. Once matched, the acoustic signal generated by the circular coil was recorded with an AKG C214 microphone. Both the microphone and coil were placed in an acoustically isolated chamber to reduce background noise and isolate the coil sound from the sound generated by the device during the pulse. A second stereo matched AKG C214 microphone recorded noise in the room so the acoustic isolation could be validated. "qTMS" denotes recordings from a prototype coil according to this invention. "Magstim" is a commercial 90 mm round coil.

Figure 14:
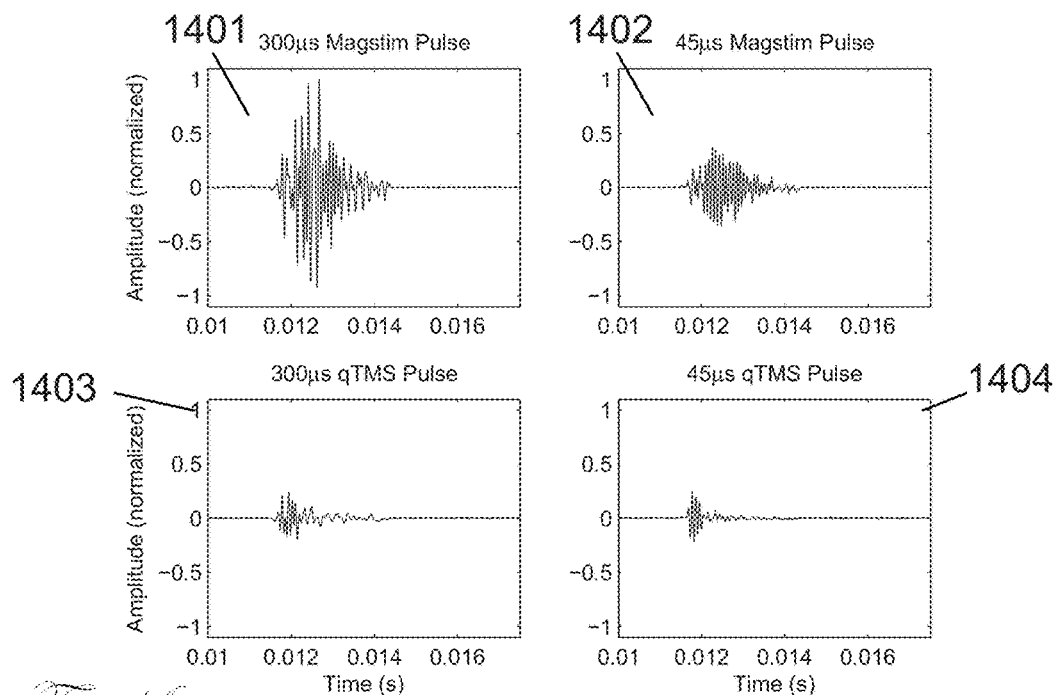

FIG. 14 shows corresponding sound recordings for the electric pulses (waveforms) of FIG. 13.

Figure 15:
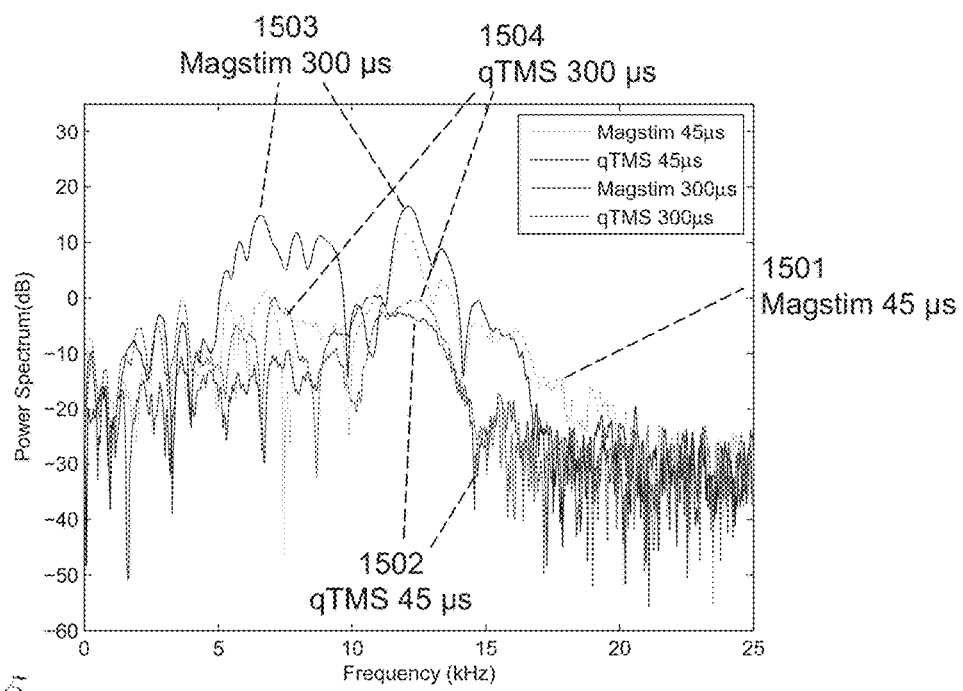

FIG. 15 shows corresponding power spectrum densities for the electric pulses (waveforms) of FIG. 13 and the corresponding sound recordings of FIG. 14.

Figure 16:
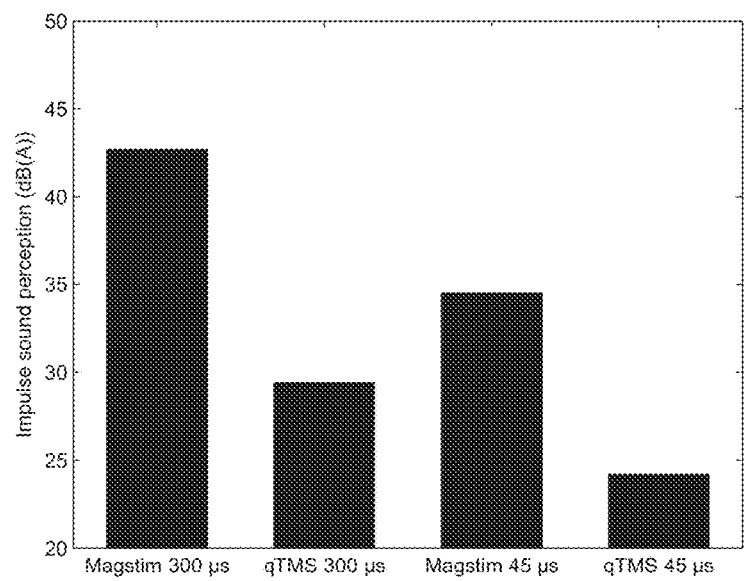

FIG. 16 compares corresponding the sound pressure levels (so-called equivalent average sound pressure level, $L_{eq}$, after A-weighting) of the electric pulses of FIG. 13.

Figures 17, 18:
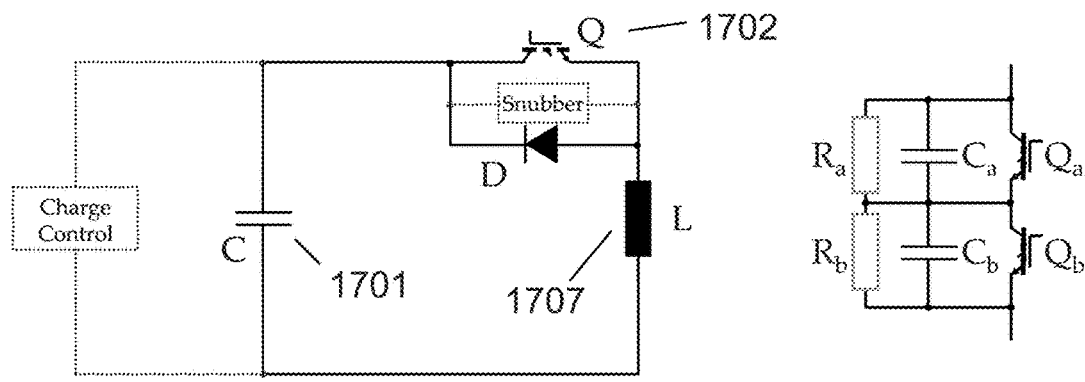

FIG. 17 shows a topology that can generate ultrabrief TMS pulses. It represents a biphasic topology in which the thyristor switch is replaced by an IGBT (1702), which at present allows significantly higher current dynamics that are required for ultrabrief pulses. Future thyristor generations may enable their employment for ultrabrief pulses too. One important disadvantage of this topology is the fixed pulse with predetermined pulse width and, thus, spectral characteristics.

FIG. 18 illustrates how two or more semiconductor switches can be combined in series in order to increase the total voltage rating. The additional passive components form a balancing network which ensures that the total voltage across the single semiconductor switches is split into several stable, preferably equal parts. In this example, the resistors ($R_a$ and $R_b$) divide the voltage especially for static voltages, e.g., in the off-state; the capacitors ($C_a$ and $C_b$) balance the voltage division during transients, such as switching or a sinusoidal pulse. Other known approaches for series switch voltage balancing, such as antiparallel Zener diodes and transient voltage suppressors, can be used instead.

Figure 19:
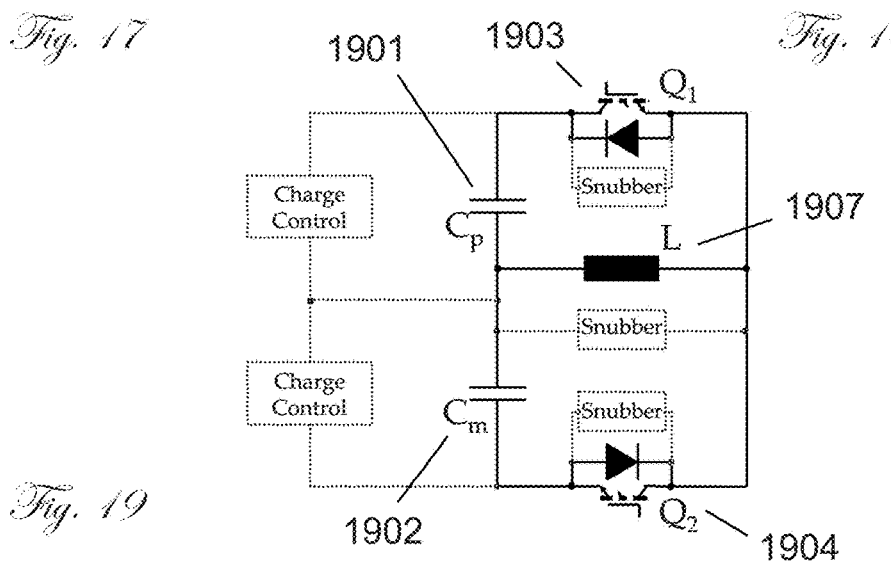

FIG. 19 depicts a cTMS technology with one half-bridge comprising two electronic switches (1903, 1904). This technology allows control over the duration of a current pulse flowing through coil L (1907) and can accordingly change the pulse spectrum.

Figure 20:
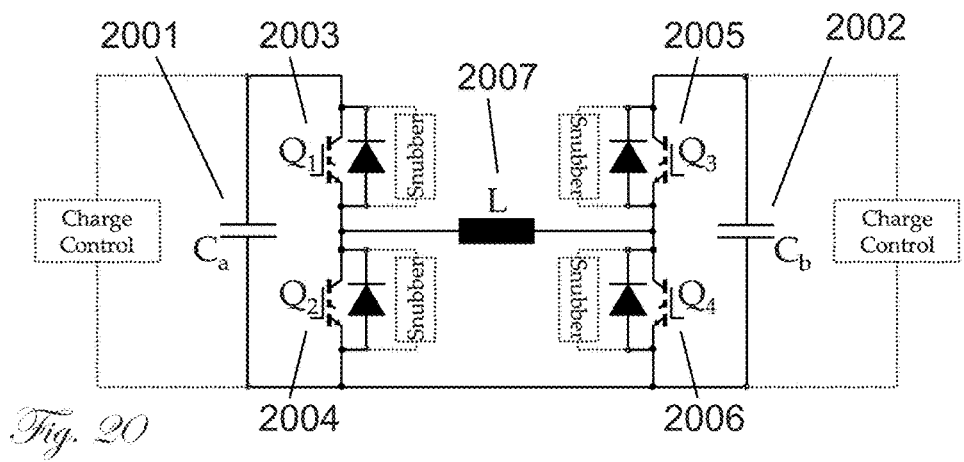

FIG. 20 shows a cTMS technology with two half-bridges each comprising of a separate pair of electronic switches (2003, 2004) and (2005, 2006) for enhanced flexibility.

Figure 21:
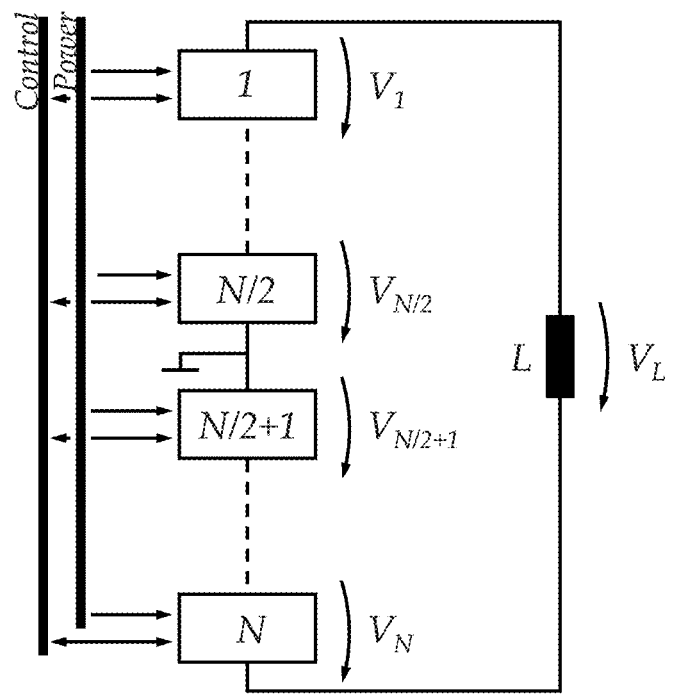

FIG. 21 illustrates the concept of a modular stimulator for generating high-voltage pulses using smaller voltage steps. The figure shows the structure of the whole circuit with N modules, a coil L, and control as well as power supply lines. The single modules can be implemented as small H-bridge circuits (see FIG. 22). The total pulse voltage is split into smaller units, each 1/N-th of the total pulse voltage. The module structure balances the circuit so that none of the circuit components in the modules, both semiconductors and passive elements such as capacitors, are exposed to more than 1/N-th of the pulse voltage. This approach enables the use of inexpensive elements with lower voltage rating. In addition, the system can quickly change between the voltage levels and synthesize pulses relatively freely.

Figure 22:
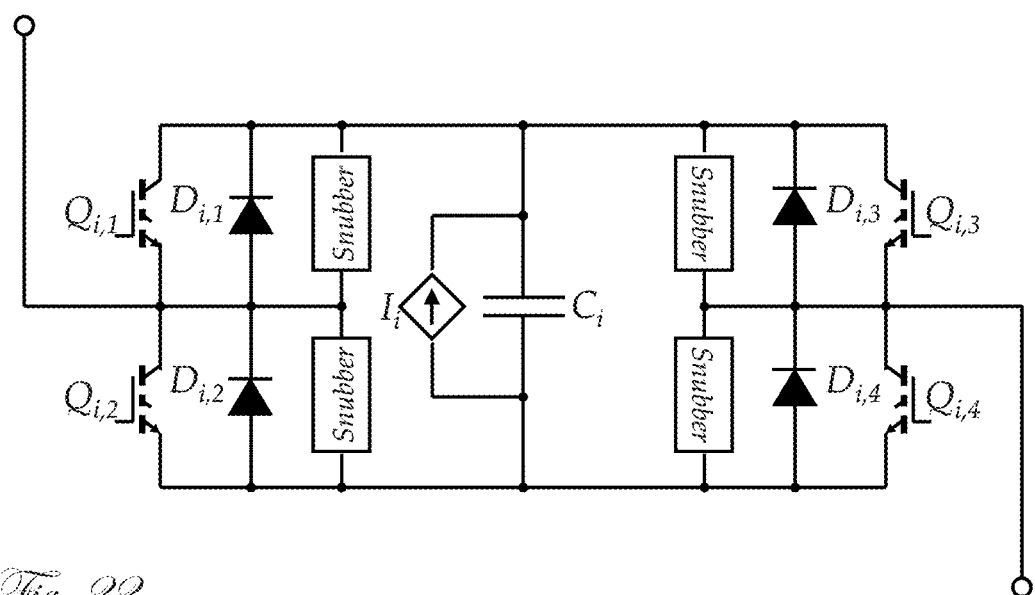

FIG. 22 shows a module circuit for the N modules in FIG. 21.

Figure 23:
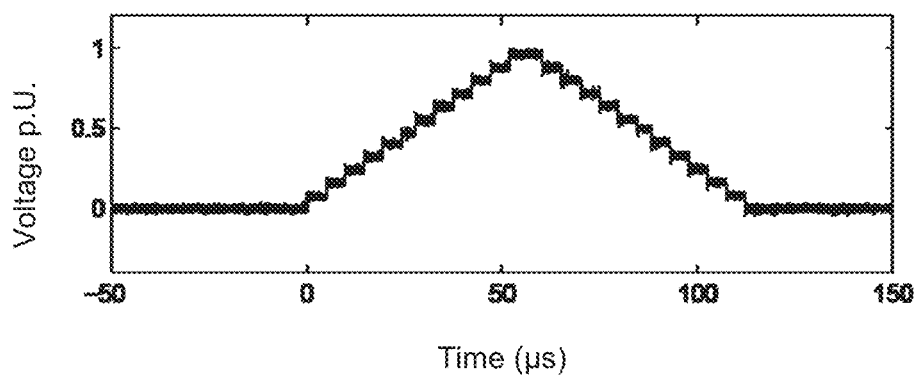

FIG. 23 shows a staircase voltage, which can be generated due to dynamic switching between the circuit levels of the modules in the circuit from FIGS. 21 and 22 and which can be modified from pulse to pulse.

Figure 24:
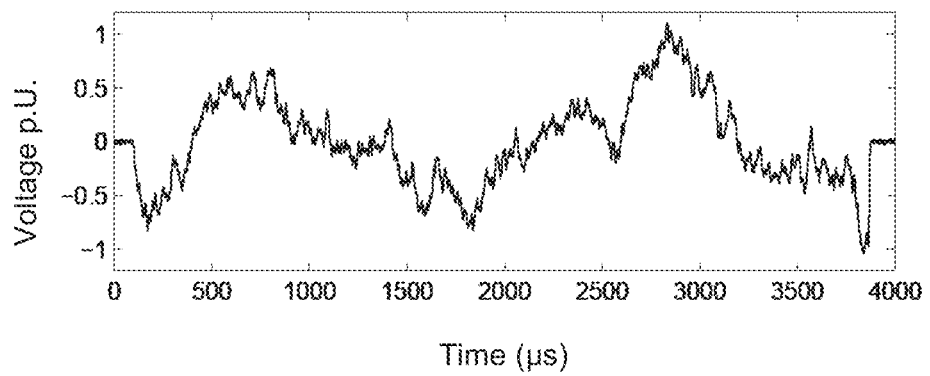

FIG. 24 shows a random-walk pulse, which illustrates the high flexibility of the circuit of FIGS. 21 and 22.

DETAILED INVENTION DESCRIPTION AND EMBODIMENTS

The objective of this invention is to reduce the noise generated by the TMS device while preserving the effective strength of neural stimulation by the TMS pulses. The quiet TMS concept consists of two key parts that can be combined but may also be used separately:

1) The first part of the strategy is to shift substantial portions of the spectrum of the TMS pulse sound to higher frequencies so that the spectral content in the range of highest sensitivity of the human ear between 500 Hz and 8 kHz is minimal, preferably they are shifted above the human hearing upper threshold of about 18 kHz-20 kHz. This approach is based on two reasons. First, the human perception for sounds above 20 kHz is negligible. Second, from a technical point of view, mechanical oscillations of such high frequencies are notably easier to suppress than those in the conventional TMS spectrum. This relates to the stronger effect of inertia, the increasing ratio of thickness of damping means and wavelength, as well as the typical frequency-dependency of the properties of materials used for the invention implementation (see point 2 below) [Moser M., Kropp W. (2010). Korperschall. Springer, Berlin/New York.]. The occupational safety limits for ultrasound exposure, on the other hand, are higher than in the audible range [Duck F. A. (2007). Medical and non-medical protection standards for ultrasound and infrasound. Progress in Biophysics and Molecular Biology, 93 (1-3):176-191.]. Third, the required TMS pulse power for such ultrabrief pulses is reduced [Barker A. T., Garnham C. W., and Freeston I. L. (1991). Magnetic nerve stimulation: the effect of waveform on efficiency, determination of neural membrane time constants and the measurement of stimulator output. Electroencephalography and clinical neurophysiology. Supplement 43:227-237; Goetz S. M., Truong C. N., Gerhofer M. G., Peterchev A. V., Herzog H. G., Weyh T. (2013). Analysis and Optimization of Pulse Dynamics for Magnetic Stimulation. PLOS One, 8 (3): e55771.]. The application of these pulses utilizes the fact the neurons can be stimulated with pulses of various shape and duration, if the pulse amplitude is appropriately scaled. For example, pulses composed of briefer electrical current phases are associated with higher acoustic frequencies. Thus, if the TMS pulse phases are made appropriately brief and if the current amplitude is selected properly, the dominant spectral components of the pulse will be above the human hearing spectrum while the pulse will still be capable of inducing neural stimulation, e.g. in the form of action potentials. A phase of a pulse is thereby a part of the electric pulse; usually a phase of a pulse denotes a part of the pulse during which the current does not change polarity and is either limited by the onset of a pulse and/or the end of a pulse and/or a change of the polarity of the current.

2) The second part of the strategy is to design all elements (coil, coil cable, and pulse generator) in such a way that, despite the very high electromagnetic energy of a pulse, (a)

only a negligible portion of the electromagnetic energy is converted into mechanical/acoustic energy, (b) the portion of the mechanical/acoustic energy that is emitted to the environment is minimized, and (c) the portion of the acoustic energy that is not emitted is rapidly converted into heat inside the device. These considerations can apply to all device elements, but are most critical for the stimulation coil, which is the major source of noise due to the high magnetic fields and electromagnetic forces, and which is closest to the operators, subjects, and patients. To accomplish objectives (a-c) the invention proposes to use several mechanical design methods, including impedance mismatching, frequency-selective decoupling with phase-shifting materials, and frictional elements for mechanical power dissipation.

Part 1: Pulse Spectrum

The first part of the strategy is to shift a substantial portion of the acoustic emission spectrum outside the hearing range, specifically to the ultrasound range (>18-20 kHz). A key determinant of the acoustic emission is the waveform of the current pulses that produce both the stimulation effect and the sound emission, due to conversion of electro-magnetic forces into acoustic oscillation. This strategy will be supported such by part 2 later that all elements have to be featured such that they do only convert a small amount of the energy content of the high-frequency oscillations back to the hearing range due to mechanical effects (e.g., inter-mode energy transfer, nonlinear effects) and thus keep the frequencies high also in the mechanical domain.

This approach is nonobvious to a person having ordinary skill in the art for the following reasons:

1) The very short electric pulse waveform does not directly entail the time course and the spectrum of the acoustic emission. Whereas conventional pulses have mostly sinusoidal current shapes resulting in pronounced spectral components with sidebands around the sinusoid frequency (see FIG. 2), sound recordings show a wide, almost flat spread of the emission throughout the whole audible range (see FIG. 15). The exact relationship between these two phenomena is not well understood. It results partly from nonlinear mechanic effects dependent on the physical properties of the used materials. Furthermore, the spectrum of standard TMS pulse waveforms (typically so-called biphasic pulses) is not monomodal and is relatively wide due to their shortness and their sharp attack/decay.

Figure 3:
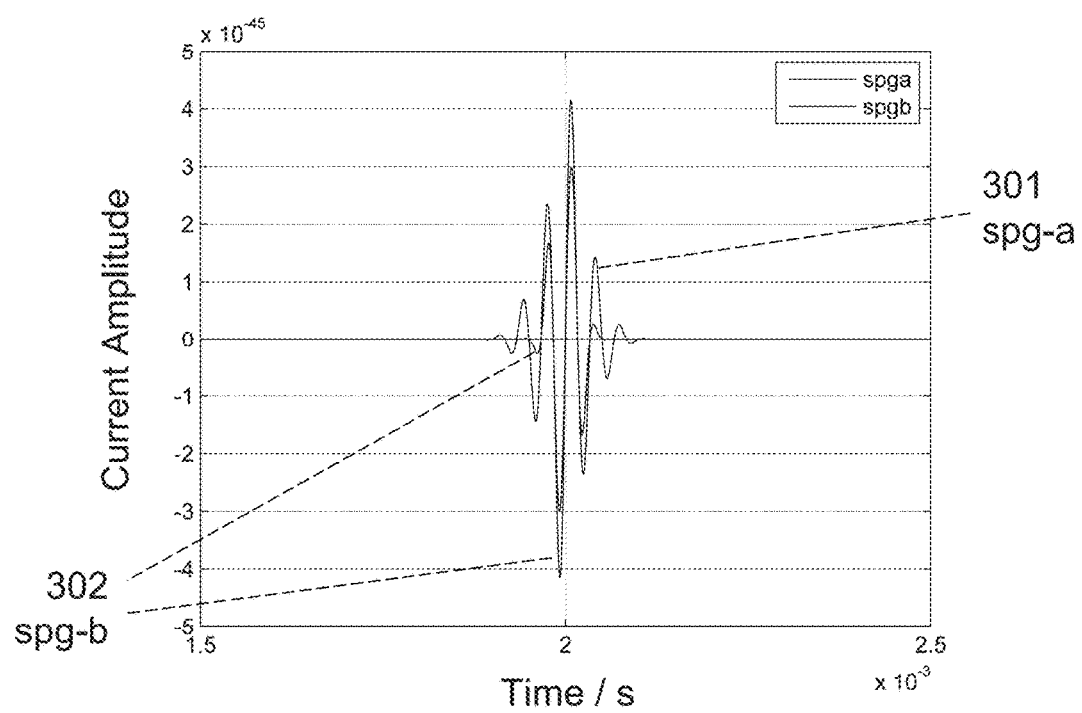
FIG. 3 shows two versions of a more acoustically advantageous current pulse waveform (301, 302), spga, spgb, according to the invention, both normalized to their approximate individual excitation threshold for a human motor neuron. In contrast to conventional waveforms in magnetic stimulation, the carrier frequency of the electromagnetic oscillation is notably higher in order to shift a substantial amount of the energy above the hearing range. Further the oscillations are not abruptly turned on and off at certain points in time, e.g. zero-current points of a sinusoidal curve with an otherwise approximately constant amplitude, but rather are modulated by a pulse envelope that softens the attack and decay of the waveform. The resulting waveforms are bandwidth-limited and do not show strong side lobes in the spectrum as FIG. 4 illustrates.
Figure 4:
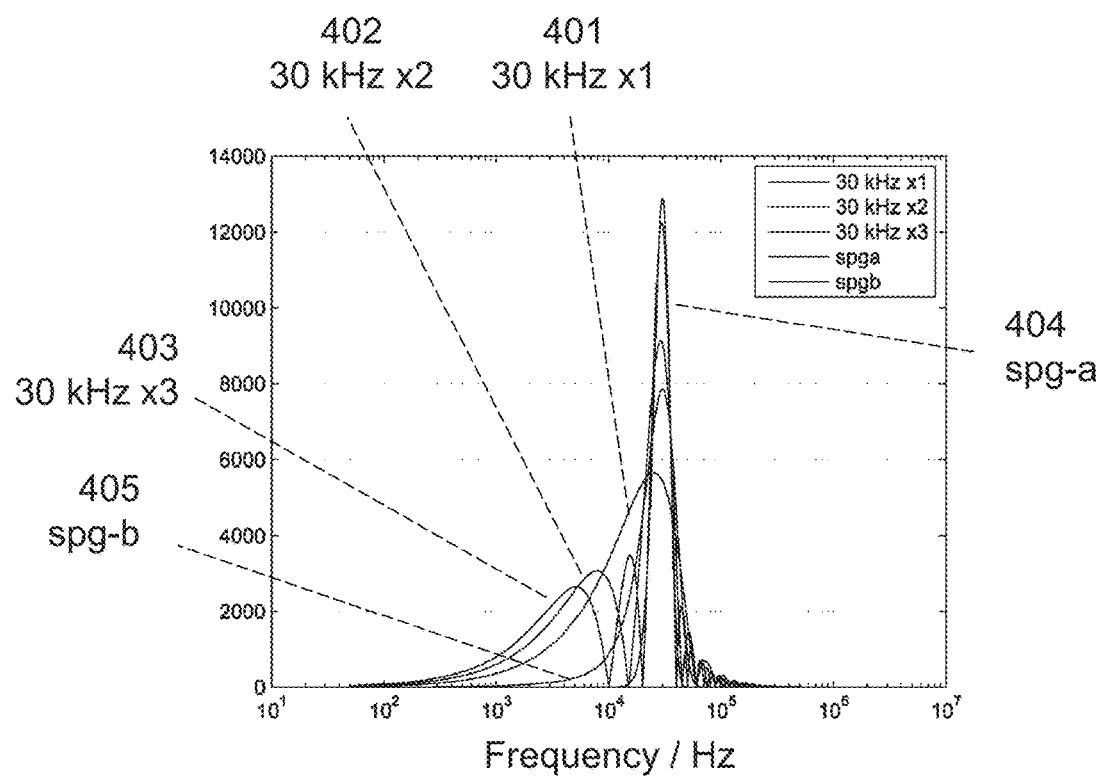
FIG. 4 shows the amplitude spectrum of the spga (404) and spgb (405) waveforms from FIG. 3 and compares them to simpler waveforms ("30 kHz×1" (401): biphasic waveform with a carrier frequency of 30 kHz, i.e., a single period of a sine current/cosine voltage; "30 kHz×2" (402): polyphasic waveform with two periods at a carrier frequency of 30 kHz; "30 kHz×3" (403): polyphasic waveform with three periods at a carrier frequency of 30 kHz). All single curves are normalized to their individual excitation threshold for comparability. The strong side-lobes of the biphasic and polyphasic pulses, which reach widely into the hearing range, are suppressed for the spga and spgb waveforms. Thus, the spectral power of the electromagnetic oscillation at lower frequencies, which in turn excites the acoustic oscillations forming the noise emission, are notably reduced compared to sinusoidal waveforms with similar carrier frequency, while preserving the neural stimulation strength. Designing waveforms with specific spectrum characteristics for controlling the sound emission of the device has been unknown in magnetic stimulation.

2) Implementing pulses with frequencies exceeding the human auditory range has not been technically feasible for magnetic stimulation. The strong currents and high voltages required for TMS are usually switched with thyristors. Thyristors, however, are limited in their capabilities to handle fast current switching. Therefore, existing TMS devices produce pulses that are almost exclusively in the range from 1 kHz to 3 kHz. This range corresponds to highest auditory sensitivity in humans, and is therefore worst for noise generation. Only recently, new device technology such as insulated gate bipolar transistors (IGBTs) and metal oxide field effect transistors (MOSFETs) have allowed for shorter pulses and increased control of the waveform shape. Prior to their introduction, it was technically impossible or impractical to produce more complex waveforms than sine waves (as suggested, e.g., in FIGS. 3 and 4), which limited the ability to modify acoustic emissions by modifying the TMS pulse waveform. TMS devices capable of pulse shape and duration control had been unavailable until they were developed by the inventors [Peterchev A. V., Jalinous R., and Lisanby S. H. (2008). A transcranial magnetic stimulator inducing near-rectangular pulses with controllable pulse width (cTMS). IEEE Transactions on Biomedical Engineering, 55(1):257-266; Peterchev A. V., Murphy D. L., and Lisanby S. H. (2011). Repetitive transcranial magnetic stimulator with controllable pulse parameters. Journal of Neural Engineering, 8:036016; Goetz S. M., Pfaeffl M., Huber J., Singer M., Marquardt R., and Weyh T. (2012). Circuit topology and control principle for a first magnetic stimulator with fully controllable waveform. Proceedings of the IEEE Engineering in Medicine and Biology Society (EMBC), 4700-4703, doi:10.1109/EMBC.2012.6347016.].

3) This approach is not trivial since waveforms with mostly high-frequency content above the hearing range enter a range that was considered not well suited for inductive neurostimulation, i.e. TMS [Litvak E., Foster K. R., and Repacholi M. H. (2002). Health and safety implications of exposure to electromagnetic fields in the frequency range 300 Hz to 10 MHz. Bioelectromagnetics, 23(1):68-82.]. However, the inventor's findings [Goetz S. M., Truong C. N., Gerhofer M. G., Peterchev A. V., Herzog H. G., Weyh T. (2013). Analysis and Optimization of Pulse Dynamics for Magnetic Stimulation. PLOS One, 8 (3): e55771.] show that this might have partly been a misinterpretation. Furthermore, noise emissions and handling of sources slightly above the hearing range are also not well-established in classical sound engineering and technical acoustics. Mechanical properties of most materials differ from their behavior in the acoustic range. Both make an increase of the frequency difficult.

4) Due to their shortness and their sharp onset, known waveforms in magnetic stimulation, and especially the subset that could also be generated with established technology, have a relatively wide spectral bandwidth. Accordingly, shortening the pulse was generally considered neither technically justified nor effective in reducing sound emission. The inventors' experimental and theoretical research supports that the sound is mostly driven by the current shape which falls with increasing frequency when comparing acoustic emission at the stimulation threshold of a nerve.

Figure 2:
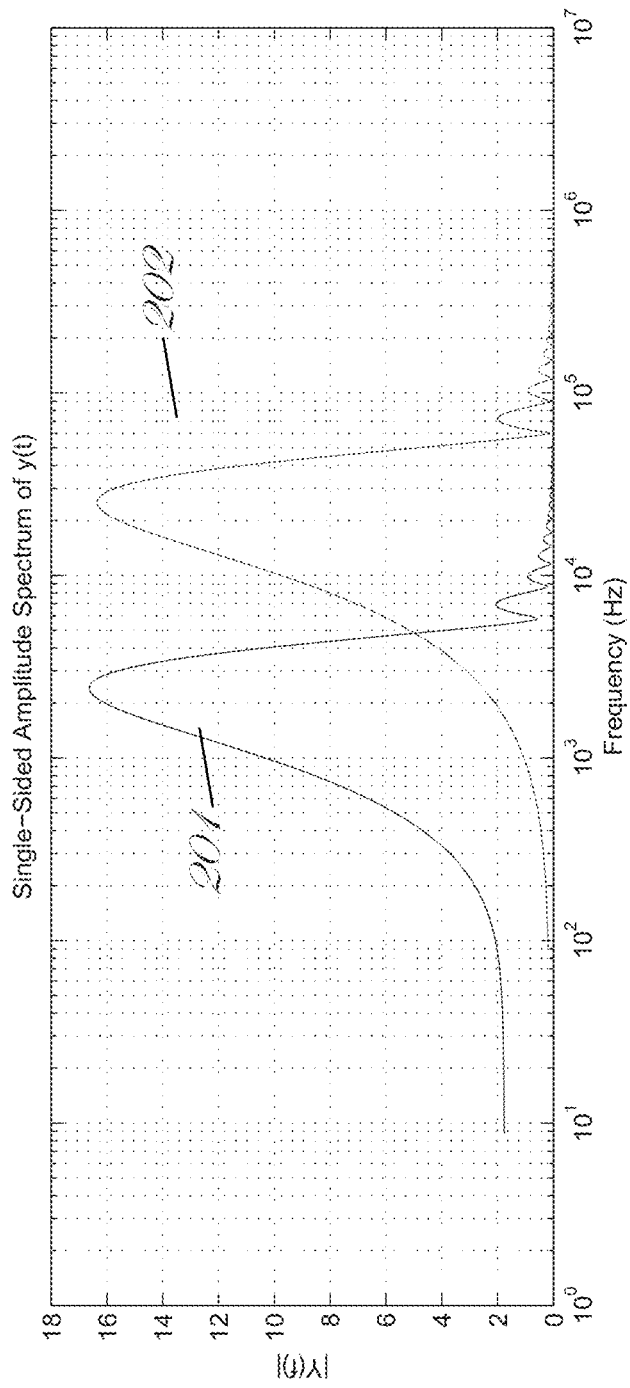
FIG. 2 shows the magnitude spectrum of the threshold coil current of a conventional biphasic Magstim figure-8 pulse (201, black) and a 30 kHz biphasic pulse (203, grey).

The objective to reduce the audible noise of TMS can be approached by making the magnetic pulse, which is generated by the current pulse, briefer, so that the fundamental frequency and dominant frequency of the magnetic pulse is above 18-20 kHz (see FIG. 2). Due to the well-known strength—duration properties of neural response, this requires the amplitude of the pulses to be increased in order to achieve neural stimulation. This, in turn, requires the TMS coil peak voltage and/or current to be increased as shown in FIG. 1.

The magnitude spectra in FIG. 2 compare the coil current of a conventional biphasic pulse (black) to that of a matched pulse with a carrier frequency of 30 kHz. Both stimuli were computationally matched to show approximately the same neural stimulation effect. Although the peak spectral power is similar for both pulses, the spectral content in the hearing range is notably reduced for the 30 kHz pulse compared to the conventional approach, which has its spectral peak in the range of maximum auditory sensitivity between 0.5 kHz and 2 kHz. FIG. 16 demonstrates the theoretical prediction that the loudness of the emitted sound is significantly reduced for briefer pulses by comparing experimentally a pulse with a duration of 45 µs and a typical 300 µs pulse that are both amplitude adjusted to produce the same effective neurostimulation strength.

An advantageous embodiment of the invention incorporates several refinements of this approach. Instead of a sinusoidal biphasic pulse with increased carrier frequency— which is essentially a sinusoidal oscillation that is stopped after one period—the number of oscillations can be increased. Those multiphasic or polyphasic pulses both reduce the neural excitation threshold [Emrich D., Fischer A., Altenhofer C., Weyh T., Helling F., Brielmeier M., and Matiasek K. (2012). Muscle force development after low-frequency magnetic burst stimulation in dogs. Muscle & nerve, 46(6): 951-959; Wada S., Kubota H., Maita S., Yamamoto I., Yamaguchi M., Andoh T., Kawakami T., Okumura F., and Takenaka T. (1996). Effects of stimulus waveform on magnetic nerve stimulation. Japanese Journal of Applied Physics, 35:1983-1988.] and narrow the broad spectrum compared to the biphasic pulse (see FIG. 4).

An even more acoustically advantageous embodiment uses a class of waveforms that are amplitude-modulated oscillations with a soft fade-in and fade-out such as a Gaussian or hyperbolic secant envelopes. Such envelopes are known from bandwidth-limited ultrashort laser pulses in optics (see FIGS. 3 and 4). Furthermore, since these waveforms have a less abrupt attack and furthermore also lower peak amplitude of the magnetic field and thus of the forces for the same stimulation effect compared to the classical sinusoidal biphasic waveform, they cause fewer nonlinear effects in general. Such nonlinear mechanical effects in the single elements of a stimulation system, most importantly in the coil, are the key mechanism that transfers the inaudible part of a TMS waveform spectrum into the hearing range. Classical TMS pulse source technology cannot generate such bandwidth-limited pulses due to limitations in the circuit topology and implementation.

The generation of brief (carrier frequencies in the range of tens of kilohertz) pulses near the neural excitation threshold requires higher peak driving coil voltages and/or currents. FIG. 1 shows the required peak voltage level for sinusoidal biphasic pulses in dependence of the carrier frequency for two different coils (9 and 18 turns). A state-of-the-art nonlinear neuron model estimates a peak pulse voltage of about 10 kV for representing the amplitude range of a typical stimulator, such as the commercial Magstim Rapid device.

As outlined above, the limiting factor of the most common circuit, the biphasic topology (FIG. 17), for shorter pulses with higher voltage is the commonly implemented thyristor switch. Present IGBTs, in contrast, allow about 300 times higher current rates of change. This increase of speed accommodates the approximately 10 times shorter ultrabrief pulses compared to conventional TMS pulses. Accordingly, the oscillator design, which consists of a pulse capacitor, a switching block, and a stimulation coil, can be used for generating the proposed ultrabrief pulses by reducing the product of coil inductance L and source capacitance C.

In a preferred embodiment, the ultrashort pulses of the invention are generated with an oscillator circuit including a pulse capacitor, an electric switch, and a stimulation coil, while the electric switch contains at least one IGBT and while the product of coil inductance L and capacitance of the pulse capacitor C is smaller than 150 microhenry times microfarad.

Whereas an increase of the voltage rating is relatively straight forward for passive components such as the pulse capacitor, the prices of semiconductor switches increase over-proportionally with voltage.

Therefore, to enable the use of cheaper switches with lower voltage rating, known techniques for operating two or more switches in series may be applied (see FIG. 18). Typically, such approaches balance the voltage across every single semiconductor to compensate for production differences, such as unequal leakage current, and variations in the timing of switching. Common approaches use resistive voltage dividers ($R_a$ and $R_b$) for static balancing and capacitive voltage dividers ($C_a$ and $C_b$) for transient balancing.

A number of TMS technologies of the inventors (FIG. 19, 20, 21, 22) enable for the first time the generation of ultrabrief pulses with sufficient voltage and with various more efficient waveform shapes. For example, the pulses in FIG. 13 were generated with the so-called cTMS technology depicted in FIG. 19 [Peterchev A. V. (2010). US 2012/0108883, EP2432547]. The cTMS topology in FIG. 19 consists of a half bridge with center-tapped capacitors $C_a$ and $C_b$. This topology can actively switch between the pulse phases by commutating the coil L between capacitors $C_a$ and $C_b$ via switches $Q_1$ and $Q_2$. Accordingly, the pulse duration and the dominant carrier frequency can be changed by the control software determining the timing of $Q_1$ and $Q_2$. To increase the frequency of all waveform phases equally, capacitors $C_a$ and $C_b$ should have similar voltage limits. The cTMS concept is further extended in FIG. 20. The two half-bridge circuits ($Q_1$-$Q_2$ and $Q_3$-$Q_4$) enable a piecewise generation of the waveform with the voltage levels of the capacitors $C_a$ and $C_b$, with their voltage difference, as well as with the zero voltage level occurring when the two coil terminals are shorted via switches $Q_2$ and $Q_3$. The important advantages of these two circuits is that they (a) can provide rectangular voltage pulses, which are more efficient than sinusoidal TMS pulses and notably reduce the required peak voltage for stimulation [Goetz S. M., Truong C. N., Gerhofer M. G., Peterchev A. V., Herzog H. G., Weyh T. (2013). Analysis and Optimization of Pulse Dynamics for Magnetic Stimulation. PLOS One, 8 (3): e55771; Peterchev A. V., Jalinous R., and Lisanby S. H. (2008). A transcranial magnetic stimulator inducing near-rectangular pulses with controllable pulse width (cTMS). IEEE Transactions on Biomedical Engineering, 55(1):257-266; Peterchev A. V., Murphy D. L., and Lisanby S. H. (2011). Repetitive transcranial magnetic stimulator with controllable pulse parameters. Journal of Neural Engineering, 8:036016.], and (b) allow changing the pulse duration, which, in turn, controls the spectrum of the waveform (the pulse duration can be controlled individually for each pulse in a sequence of pulses).

To reduce the required pulse source voltage (up to ~10 kV) to the range where semiconductors are more cost-efficient (up to ~3.3 kV), an output transformer can be used for all of these topologies. The coil inductance can be maintained in the typical range of about 8 µH to 25 µH in order to reduce losses caused by an otherwise (for lower coil inductances) high current in the cable and a low ratio of coil inductance and parasitic inductances in series with the coil.

Another approach to handling the high peak voltages and currents required for ultrabrief TMS pulses is to implement the pulse source with a modular circuit topology depicted in FIG. 21. As shown in FIG. 21, the total pulse voltage is equal to the added outputs of multiple individual modules. The individual modules can be implemented, for instance, as H-bridge circuits (see FIG. 22). This technology divides the total high pulse voltage across smaller units [Goetz S. M., Pfaeffl M., Huber J., Singer M., Marquardt R., and Weyh T. (2012). Circuit topology and control principle for a first magnetic stimulator with fully controllable waveform. Proceedings of the IEEE Engineering in Medicine and Biology Society (EMBC), 4700-4703, doi:10.1109/EMBC.2012.6347016.]. With these smaller units, the system can synthesize a waveform by using voltage steps as illustrated in the recording in FIGS. 23, 24. For a system with n modules (FIG. 21), the total pulse voltage is divided by n for each module and dynamically balanced so that the system can use inexpensive low-voltage components for the switches and the capacitors.

This topology can be interpreted as a high-power digital-to-analog converter and can accordingly generate almost any waveform. Therefore, this design can synthesize acoustically advantageous waveforms such as the band-width-limited polyphase pulse with Gaussian or hyperbolic-secant or similarly smooth temporal envelope shown in FIG. 3. All possible envelopes have in common that they have a maximum level from which they decrease monotonically towards zero on both sides with a derivative whose absolute value does not exceed a finite predefined limit. A reasonable limit is the amplitude of the envelope divided by the period length of the polyphasic pulse.

Part 2: Coil Acoustic Properties

Whereas part 1 of the invention strategy explained how the acoustic emission can be reduced by using appropriate pulse shapes, part 2 covers the mechanical design of the system. This includes the conversion of electromagnetic energy into the mechanical domain, propagation, conversion into heat, and emission as airborne sound and body sound, i.e., the clicking usually associated with TMS pulses. As already mentioned, the mechanics have to meet two requirements. First, conversion and acoustic emission should be minimal. Second, in case it is combined with part 1 of the invention strategy, the sound spectrum of the click should be kept above the hearing range. This includes minimizing mechanical nonlinear effects, which generate new frequency components due to waveform distortion. Further, the frequency-dependent acoustic impedance design should be such that all acoustic oscillations in the hearing range are kept inside the TMS device (including the coil) so that they can be converted to heat there.

The sections below split the full path of the acoustic waves into several stages that have to be handled with different methods. The acoustic path spans the source (all parts which immediately conduct the pulse current) to the device surface, where it couples mechanically as body sound to the subject/patient and as airborne sound to the environment. The most important device elements in terms of emission are the coil and the coil cable because of the strict space and weight limitations relevant to their design. The pulse source, on the other hand, can be damped easily with classical noise reduction means. Although the text focuses on the coil as an example, the invention can be applied to all elements of a stimulation system.

Principle

The coil design splits the acoustic pathway systematically into three sections. (1) The acoustic source in a coil is the electrical conductor that vibrates in consequence of the magnetic forces generated by the high pulse currents. The key mechanism of the source is a conversion of a part of the electrical pulse energy into mechanical energy; this conversion should be minimized. (2) Further, the transmission of the sound power (reduced by (1)) to the surface, where it is emitted to the environment as airborne and body sound, has to be inhibited. (3) Instead, a substantial portion of the sound could be suppressed by converting it into heat by a dedicated section located inside the coil. Based on this partitioning, the invention proposes to reduce the total sound emission by engineering the mechanical impedances with the help of impedance mismatching, phase-shifting elements (materials with high elasticity and mass density), as well as (phase-neutral) frictional material properties (viscoelasticity).

At the coil conductor, the system can be treated as a power converter that couples two domains, the electromagnetic and the acoustic. In contrast to classical sound engineering where the noise source usually may not be changeable, the conversion process can be included in the approach for TMS devices. The sound sources in magnetic stimulation devices are the conductors that carry the high stimulation pulse current. Due to electromagnetic forces within and between conductors, some of the electrical energy is converted into acoustic energy. To minimize this conversion so that further damping only has to handle a minimum amount of acoustic energy, the acoustic impedances are mismatched on purpose. The sound source (i.e. electro-mechanical converter) is pressure-driven (equivalently to a synchronous motor below the breakdown torque). This implies that the mechanical pressure amplitude on the conductors is almost constant while the resulting displacement depends on both the pressure and the mechanical impedance. Accordingly, the invention proposes forming a high mechanical input impedance to the incoming acoustic oscillation for minimum conversion. Furthermore, this step can be used to suppress especially lower-frequency modes in the audible spectrum as described below. Thus, nonlinear transformation of the high-frequency excitation into audible components can be further reduced.

Conversion

Key aspect of designing the first section of the acoustic pathway is the reduction of the electrical energy conversion into acoustic oscillations. First, this step minimizes the amount of energy that has to be damped. Second, this not converted amount of energy remains on the electrical side and is no longer part of the losses, thus increasing the device efficiency.

The conversion efficiency is essentially a mechanical impedance problem. The conversion of electric energy into acoustic vibration takes place at the high-current conductors in the coil, the pulse source, and the cable in between which start to vibrate due to alternating magnetic forces. In conventional TMS systems, the electrical side is formed by a high-voltage high-current oscillator with low impedance and relatively low mechanical energy loss. Future TMS technologies that do not implement a simple oscillator may most likely behave similarly. Therefore, the conductors act as mechanical pressure sources. Consequently, from the mechanical side, the electric source can be assumed inexhaustible. Thus, all damping means, which usually aim at converting vibrations into heat, have to be avoided to achieve a low conversion factor. Similar to a voltage source which is connected to a low load resistance, the acoustic pressure would be reduced only minimally, while the sound velocity—as the acoustic equivalent to the electrical current—and therefore the acoustic energy that enters the mechanical domain grows strongly. Only very high damping could deplete the source energy so that the sound emission would decrease again. However, this would in most cases also mean that almost the entire electrical pulse energy of the TMS system would have to be converted into the mechanical domain.

In the approach according to the invention, the conversion is therefore actively reduced by increasing the mechanical impedance in one or both of the following ways:

(a) The mechanical stiffness of the conductor compound is increased. This measure prevents especially the emergence of low- and medium-frequency acoustic components. Since for constant power, the acoustic sound velocity falls approximately with the inverse of the frequency and since the stiffness of most materials falls nonlinearly with frequency (i.e. the mechanical impedance is increased with frequency), the effect of stiffness is reduced for higher frequencies. Despite that, the higher stiffness shifts the conversion range to higher frequencies, suppresses the conversion of spectral side bands, and obstructs the formation of audible low-frequency components by nonlinear effects. Methods to increase the stiffness of the conductor are, for instance, the use of bimetal structures of copper (or another electrically well conducting material) and a stiffer metal, a strained conductor embedded into a stiffer material, stiffening elements such as beams, and/or different conductors or parts of the conductors bonded to each other with rigid structural adhesives. One suitable stiffening material is steel which has about four times higher E-modulus (Young's modulus) then copper [Moser M., Kropp W. (2010). Korperschall. Springer, Berlin/New York.]. Thin flat wires as used in several commercial coils are suboptimal without rigid stabilization. For the approach of increased stiffness, the frequency response follows approximately 6 dB Id(f)/Id(E) with the frequency f, the stiffness E, and the dual logarithm Id. Furthermore, most real materials have a frequency-dependent stiffness, usually increasing with frequency [Moser M., Kropp W. (2010). Korperschall. Springer, Berlin/New York.].

(b) The mass of the conductor compound is enlarged in order to increase inertia. Whereas stiffness blocks especially the conversion of lower frequencies and shifts the frequency response as well as potential resonances to a higher frequency range, the mass limits the spectrum at the upper range by counteracting fast displacement. If the electromagnetic spectrum of the TMS pulse is chosen to be mostly in the high-frequency range, the effect of the increased mass would be further enhanced. The frequency characteristics of the impedance resembles an exponential growth with a growth rate of 6 dB/[Id(m) Id(f)] with the mass m and the frequency f.

Ways to increase the effective mass are appropriate material selection and/or increased volume. Accordingly, a high cross section of the conductor and high-density materials are useful. Fully replacing copper by denser conductors may not be economic though, because the conductance of these stiffer materials are notably smaller than that of copper (by factors of two to about ten). Therefore, these stiffer materials are most advantageous in places of the conductor where the current density is low, e.g., due to given high-frequency effects.

Propagation

A second aspect of the acoustic pathway design is to reduce the propagation of the acoustic oscillations to the surface, where they are emitted to the air as sound or to the subject as body sound.

For the frequency range, the size, and the characteristic wave speeds of the materials of TMS coils, the dominant mechanical modes are represented by bending oscillations. Transversal shear and longitudinal pressure waves occur mostly at the lower and upper end of the relevant spectrum, where they can be effectively reduced by traditional methods.

Accordingly, the wavelength range and the propagation mechanisms of the acoustic emission have to be taken into account. These depend on the geometric extensions, the material properties (wave speed for the specific type of oscillation), and the excitation frequency, which is determined by the electromagnetic waveform. For the typical conditions in TMS, the dominant components are usually represented by bending waves. In addition, higher frequency components can emit surface waves. Only in the lower frequency range of the oscillations and mostly for smaller coils, the coil can act as a point source. In this case instead of surface bending the whole body shows almost uniform oscillations in the form of translation or contraction/expansion, and becomes similar to a loudspeaker. For the materials and compact structure of coils, such point-source behaviour may only occur at the low side of the human hearing spectrum below 1 kHz.

Consequently, the material layers do not only present a specific impedance on the path from inside to the outside, i.e., the source to the environment, but also perpendicular to that direction, along the layer. Acoustic energy flow in this direction is a consequence of the inhomogenous instant sound pressure conditions due to different modes. A deliberate use of material properties, such as stiffness, mass, viscosity, and elasticity is used in this invention to address the different sound components. In an oversimplified picture, stiffness and viscosity, for instance, are most effective for the dominant bending oscillations/waves, whereas inertia obstructs the low-frequency point-source-like components.

The phase-shifting, capacitive nature of an elastic path to the surface decouples the coil winding block (core) and inhibits with a low-pass behavior the transmission of the acoustic energy to the surface of the coil. Dissipation of the trapped mechanical energy is achieved in a stiff viscoelastic layer that can cover the acoustic source (the core conductor). Without affecting the core mechanical impedance, it converts oscillations into heat as a shunting resistive path.

Layer Thickness, Insulation, and Safety

The TMS coil conductor can be encased in high-voltage electrical insulation. The acoustic materials can also act as electrical insulation. A thicker insulation material between the coil and the subject's head can improve the acoustic characteristics of the coil. However, an increase of the insulation thickness would require higher pulse amplitudes for stimulation and accordingly more noise generation in the winding. Therefore, the viscoelastic and elastic layers on the face of the coil toward the subject should only have thickness around a millimeter each. On the other hand, towards the edges of the coil face and on all other sides, the traditional stimulation coil designs such as the figure-of-eight and round configurations can accommodate thicker insulation.

As in traditional TMS coil design, the coil insulation has two aspects. The insulation between the single coil turns is not safety-relevant and may therefore be a single basic insulation according to IEC 60601. Usually, insulation materials are furthermore chosen to be arc resistant (e.g., Level 4 according to VDE 0303) to avoid side-effects of a potential brake-down. For all proposed mechanical materials, potting products with a dielectric strength of more than 20 kV/mm are available including elastic silicone 25 kV/mm; high-stiffness epoxy compound 33 kV/mm; PU 35 kV/mm; PET 90 kV/mm; ABS 70 kV/mm. Therefore adjacent turns exposed to only a portion of the total voltage (less than 1 kV) can be insulated sufficiently by a core potting. At locations where turns with higher voltage difference meet, an insulation of up to 1 mm has to be taken into account. The insulation between the conductor and the surface is considered safety-relevant and is therefore a reinforced insulation according to IEC 60601. With the dielectric properties of the materials given for the mechanical design, it is aimed at an insulation strength of more than 25 kV (AC) with an overall thickness of more than 2.5 mm. This reflects the minimum thicknesses that targeted for the mechanical construction.

Although not audible, ultrasound emission can still have negative impact on a human. However, these high-frequency oscillations are relatively easy to suppress because the effect of all three above-described means increases with frequency. The increasing efficiency is a consequence of inertia, the increasing quotient of layer thickness and the wavelength, and/or typical frequency-dependency of material properties and becomes visible in the prototypes. Therefore, the device ultrasound emissions can stay below occupational limits (110 dB+9 dB; [Duck F. A. (2007). Medical and non-medical protection standards for ultrasound and infrasound. Progress in Biophysics and Molecular Biology, 93 (1-3): 176-191; ACGIH (2001). Documentation of the Threshold Limit Values for Physical Agents. Cincinnati (Ohio).]) and public exposure recommendations (100 dB; [Duck F. A. (2007). Medical and non-medical protection standards for ultrasound and infrasound. Progress in Biophysics and Molecular Biology, 93 (1-3):176-191.]), which are both lower than the regulations for medical equipment according to IEC 60601.

Detailed Description of the Layers

As outlined, two layers, a viscoelastic and an elastic layer, reduce and guide the sound emission of the preferably stiff and heavy conductor core. Preferably, the viscoelastic layer covers the core, while the elastic layer enfolds the viscoelastic layer.

A layer or material layer according to the invention is usually a volume that is filled with at least one material of any known state of matter (e.g., also a low-pressure gas or low-pressure gas mixture), wherein the volume comprises at least one well-defined surface that forms a mechanical contact with at least one other material and wherein the interface formed by the mechanical contact has a finite area, preferably higher than one square centimeter and particularly preferably higher than five square centimeters. The interface between two materials should prevent mixing of the materials. For instance, two liquids or gases that are soluble in each other cannot form an interface according to the invention. However, two solid bodies (including materials that are subsumed soft matter, e.g., polymers, gels, foams of materials), for example, can form layers with well-defined surface areas, although slow material degradation, material diffusion, or the like from one material layer into the other may lead to a gradual material transition instead of a stepwise material transition, as long as the process of mixing at the interface during operation is slow compared to typical session durations, preferably less than 1% mass diffusion from one material into the other is occurring per hour. The minimum volume of a material layer is preferably 100 cubic millimeters. A layer or material layer does not necessarily have to be continuous but can also consist of a number of patches, which are, for instance, arranged next to each other with gaps in between. Further, a layer of material layer can contain several different materials that provide the desired overall properties (e.g., stiffness, viscoelasticity, or elasticity) in combination or of which every material has in general the desired property, but each to a different degree.

(i) Viscoelastic Layer:

The viscoelastic layer is characterized by a high viscosity q. Ideally, the latter is accompanied by a high stiffness due to a high E-modulus. The product E q achieves both impeding bending modes and converting them partly into heat, which leads to an attenuation of the sound wave entering the layer. For this purpose, it is favorable that the viscoelastic layer has a firm connection to the adjoining layer that is closer to the source. In this case, bending oscillations and waves of the core can be dissipated by frictional shear stress, which is the most efficient mode for common viscoelastic materials. Although not absolutely necessary, the effect of the viscoelastic layer can be notably improved if it is terminated by a stiff and potentially (but not necessarily) massive layer which is formed so that the viscoelastic layer is confined on both sides. The stiff winding conductors or any other stiff layer inside the coil (the core) and the additional stiff layer on the outside can significantly increase the shear losses.

(ii) Elastic Layer:

In contrast to the winding conductor which is the source of the acoustic oscillations and has constant-pressure amplitude low-impedance characteristics, the interface of the viscoelastic layer to the adjacent layers acts as a source with high inner impedance that can be depleted, i.e., its energy content is practially exhaustible. Accordingly, acoustic decoupling by a highly elastic layer is possible. The elastic layer does not hinder oscillations but acts like a mechanic equivalent of a phase-shifting capacitor in the electrical domain forming a mechanical low-pass filter. The characteristic equations of the capacitor and the elastic layer are similar: $d/dt<p>=K$ $E<v>$, where the pressure p is the voltage equivalent, the displacement velocity v is the current equivalent, E is the stiffness, and K is a proportionality factor. In case the mass/density of either or both of the two layers can be influenced, the impedance-mismatch effect can be notably increased with a high density of the viscoelastic layer. For the elastic layer, in contrast, a low density is more favorable in general.

With the elastic layer, the inner core becomes mechanically decoupled from the casing.

The efficacy of both elastic and the viscoelastic layers increases with frequency. This is additionally supported by the nonlinear behavior of the viscosity of many materials (known as dilatant properties, see [Möser M., Kropp W. (2010). Korperschall. Springer, Berlin/New York.]). Accordingly, the proposed shift of the electromagnetic waveforms to higher frequencies according to the invention simplifies acoustic damping with this approach.

For the decoupling approach to work, the elastic layer should be encompassed by inert and/or stiff layers. This can be either the casing or a repeated sequence of viscoelastic and/or elastic layers followed by the casing. To increase the mass density and stiffness of the casing, fiber reinforcement, plastic mold (such as duroplasts), acrylamid-polymer compound, ceramic, or a compound of a polymer with inorganic fillings may be incorporated.

As a first approximation, the coil scheme outlined above can be represented as a highly simplified equivalent circuit shown in FIG. 10. The equivalent circuit consists of the pressure source p, the intentionally high source impedance represented by the mass $m_s$ and the high stiffness $E_s$, the damping block formed by highly elastic (i.e., less stiff) element $E_i$ and the viscoelastic component $\eta_i$ (can be repeated), as well as the casing with its mass $m_c$ and its stiffness $E_c$.

Prototype

A prototype implementation of the coil according to the invention has 11 turns and an inductance of approximately 8 µH. This design has a relatively small number of turns, requiring higher pulse currents and lower voltages than designs with more turns. The stiff winding conductor block was formed by an annealed copper-covered steel conductor (steel core diameter: 3.5 mm; copper cast thickness: 0.85 mm; Commscope, NC) which was embedded into a high-stiffness epoxy-based polymer ($E_m$~5 $GN/m^2$, 33 kV/mm; 3M, Inc., MN). For minimum elasticity, the distance between the single turns (0.8 mm) was kept as small as possible to reduce potential elastic compression of the polymer potting. Furthermore, the conductor segments leading to the cable were used as beams to further stiffen the construction mechanically. For the viscoelastic layer, a bitumen-based PMA compound ($\eta E_m > 10^{13}$ Pa²s at 25° C.; Current, Inc., CT) was employed (1 mm at the bottom, about 7 mm on back). The decoupling layer to the casing was formed by highly elastic silicone (~0.5-1 mm bottom layer thickness, ~7 mm top layer thickness; Shore A 25, $E_m < 1$ MN/m²; Dow Chemical, MI). The casing is made of polyurethane ($E_m$~6 GN/m²; 1 mm bottom layer thickness, ~5 mm top layer thickness; Freeman Manufacturing Inc., OH).

The sound emission of the coil prototype is recorded and compared to a commercial round circular coil (90 mm, P/N 31923, Magstim Co.) as a reference. A cTMS pulse source (see FIG. 19) provides control over the pulse width and generates rectangular bipolar pulses with 300 µs and 45 µs duration (see FIG. 13). Every pair of pulse and coil was matched to the same modeled neuron response. Stimulation was modeled by an air search coil with a diameter of 10 cm centered at a distance of 2 cm from the TMS coil (representing the typical distance of the TMS coil from the cortex). The output voltage of the search coil is proportional to the electric field induced by the TMS coil and fed into a first-order, linear, short-term integrating filter with a time constant of 150 µs which is established as a neural membrane response model [Barker A. T., Garnham C. W., and Freeston I. L. (1991). Magnetic nerve stimulation: the effect of waveform on efficiency, determination of neural membrane time constants and the measurement of stimulator output. Electroencephalography and clinical neurophysiology. Supplement 43:227-237.].

As the sound recordings in FIG. 14 show, in all cases the acoustic response is notably longer than the electromagnetic pulse. As discussed, for both the conventional coil and the prototype coil the shorter pulses reduce the sound amplitude. This observation does not take into account the human hearing range which will further attenuate the higher frequencies associated with the shorter pulse. In the conventional coil, the reduction in sound amplitude can be explained by the increase with frequency of the conversion impedance. The conversion impedance is approximately proportional to the product of mass and frequency in this frequency range. For both pulse durations, the novel coil concept can notably reduce amplitude and duration of the clicking sound. The latter is especially important since the human sensitivity falls approximately exponentially with duration for sounds shorter than about 200 ms. The novel coil shows notable reductions in the sound spectrum corresponding to the most sensitive range of the ear below about 10 kHz (see FIG. 15).

Further Embodiments

The two main embodiments of above-described concept for a quiet mechanical design differ in how the individual elements are implemented, especially of the winding conductors. Differences in the performance are also dependent on the frequency range and the dominant type of acoustic modes.

In the first embodiment (see, e.g., FIG. 5) several or all turns of the winding conductor are combined in a stiff block. The individual turns are closely connected, e.g. embedded into an epoxy matrix. Since the compressing forces on a conductor are pointing towards its neighbors, it is furthermore an option to provide a tight mechanical contact between the turns and/or to provide higher rigidity with strained conductors.

This stiff winding block suppresses mechanical motion and increases the input impedance from the perspective of the electrical pulse source and the pressure source as the secondary side of the electromechancial converter. The whole winding block is subsequently dampened and decoupled by a combination of viscoelastic and elastic layers, which may be repeated, as described above. The casing may follow either an elastic or a viscoelastic layer. The advantages of this embodiment are that the winding conductor block, which acts as an acoustic source, can be reinforced easily with various types of known means, such as beams, reinforcing fibers (e.g., glass or polyamides) and appropriate conductor shapes so that potential acoustic modes or windows are shifted to higher frequencies. The whole winding conductor block is relatively compact and does not require extensive space. However, the tight spacing between the individual turns requires a proper electrical insulation, which can impede the stiffness.

In a second embodiment (see, e.g., FIG. 8), every single turn is decoupled separately. Accordingly, every turn is encompassed by at least one viscoelastic and (optionally) one elastic layer. In contrast to the above-described first embodiment, this approach requires more space but is less critical in terms of electrical insulation between turns and a potentially not stiff enough mechanical interconnection of individual turns. The insulation requirements can be important for ultrabrief, high-frequency pulses with a substantial portion of the electromagnetic pulse spectrum above the hearing range, which requires relatively high voltages of several kilovolts as explained above.

Furthermore, the decision between these two embodiments depends further on the acoustic conditions, which are influenced by the electromagnetic pulse, the material selection, and the geometric conditions in the following way. In case the material-dependent wavelength of the acoustic oscillations is notably lower than the geometric extensions of a single conductor, the local oscillations can elicit propagating waves. In consequence, a tight connection of single turns in order to form a bigger block can no longer significantly increase the acoustic resonances or response window as it does for standing oscillations without propagating waves.

Furthermore, these two embodiments can form a hybrid to combine advantages of both. In that embodiment, every individual turn has a separate dedicated instance of at least one of the two layers, either the elastic or the viscoelastic layer, as in the second embodiment. In addition, two or more (and potentially all) turns share the remaining layer as in the first embodiment.

In a preferred embodiment, both embodiments can be significantly improved by further increasing the source impedance. As is extensively described above, the source impedance can be raised by increasing the stiffness (described by the E-modulus) and/or the mass, m. Since the high electric conductance of copper might be advantageous in the conductor, additional compounds can be used to change the material properties. Whereas this can also be achieved in alloys, potentially with spatially heterogeneous materials, the preferred embodiment favors bimetals and copper-clad metals. Such conductor compounds are formed by two or more metals—of which one is copper oder a similarly well conducting materials (such as silver and gold) with certain purity—that are tightly bonded. This tight connection can be formed with known methods, for example by different welding techniques or chemical approaches such as electroplating.

Such copper-clad wires are used to save copper in many applications in power engineering. In order to increase the stiffness of the conductors, another preferred embodiment uses copper-clad steel conductors. These conductors and the interfaces between the single, usually metallic, components can be chosen in any desirable geometric shape.

For this embodiment, the copper content is preferably distributed geometrically in such a way that it reflects the inhomogeneous local current distribution in the cross section of the conductors due to the skin and the proximity effects in order to provide the highly conducting copper at locations with highest current density. Thus, the effective conductance of the total conductor is only marginally affected despite a large effect on the acoustic emission. Alternatives to steel are molybdenum and tungsten, which provide higher E modules and mass densities. In addition to the increased total stiffness of the conductor, the different E-modulus of the components in such a composite lead to different acoustic sound wave speeds, and can therefore break modes of standing waves. Furthermore, the material costs for a coil, which are dominated by copper, are reduced.

Since the frequency components of the electromagnetic pulse are relatively high so that the skin and the proximity effect play a notable role, the conductor can in another preferred embodiment furthermore be split into smaller subregions or strands, as known from the design of high-frequency litz wires, so that the total cross section of the conductor is divided into smaller units that are either electrically insulated against each other or poorly connected. The litz wire principle reduces the frequency-dependent increase of the conductor resistance and can be achieved in this application by structuring the conductance of the wire into cross-sectional compartments of different conductivity. The two or more components of the composite wire, e.g. copper-clad steel, can be structured such that the electrically highly conductive material forms multiple independent paths along the conductor that are embedded into the electrically less conductive but usually mechanically stiffer compound, similar to a litz wire with many insulated filaments.

Alternatively, another preferred embodiment uses a high-frequency litz wire. In that embodiment, the concept proposed above that the coil winding (acoustic source) should be stiff, suggests that the litz wire should be made as stiff as possible. This can be achieved, for example, by appropriate embedding in a stiff material such as a ceramic material or a polymer. Furthermore, the individual filaments of the litz wire can themselves be compounds, for example copper-clad steel. In that case, the individual filaments achieve a relatively high stiffness due to the material properties.

In another embodiment of the invention, although less potent, a notably reduced sound emission compared to known approaches can also already be achieved if only one of the two means, i.e. the viscoelastic layer or the elastic layer, is implemented. In this embodiment, the reduction of the sound emission concentrates on one of the mechanisms, either decoupling of the core from the casing or increasing mechanic loss. A reduction of the conversion of electrical energy into mechanical by increasing the mechanical stiffness and/or the mass density and/or the mass of the core is also in that case highly recommended.

Another embodiment is a method for the stimulation of neurons and/or mycocytes, wherein current pulses generate magnetic field pulses that in duce stimulating electric currents in body tissue by electromagnetic induction, wherein the stimulating electric currents trigger action potentials of the neurons and/or myocytes, and wherein the magnetic field pulses are generated by a coil that can be placed close enough to the body tissue that the magnetic field generated by the coil can permeate the body tissue, and wherein the magnetic field pulses have a temporal shape that corresponds to the temporal shape of an electric current flow through the coil, and wherein the temporal shape of the current is chosen such that less than a quarter of the energy of the current is in the spectral range between 500 Hz and 18 kHz.

Another embodiment of the invention generates short and strong current pulses with a total duration of less than a millisecond in at least one coil such that the at least one coil generates magnetic field pulses with a magnetic flux density between 0.1 and 10 Tesla, which induce electrical currents in body tissue according to the principle of electromagnetic induction, which evoke action potentials in neurons and/or mycocytes, wherein the at least one coil is designed such that it can be positioned near the body tissue to be stimulated such that the generated magnetic field can permeate the body tissue; and wherein the device contains at least one capacitor for storing Energy that is required for the magnetic field pulses; and wherein the electric currents induced by the at least one coil in the body tissue at least one tenth and at maximum tenfold the current required for evoking action potentials in neurons and/or myocytes. This embodiment is further designed such that at least one electric conductor of the at least one coil and/or at least one electric conductor of at least one electric connection cable that connects to the at least one coil is embedded into a mechanically stiff polymer and/or a mechanically stiff synthetic material and/or a mechanically stiff composite material and/or a mechanically stiff ceramic material and/or a mechanically stiff glass forming a stiff unit able to reduce the sound that is emitted by the at least one coil and/or the at least one electric connection cable as a result of the strong current pulse.

In a preferred embodiment, the sound emitted by the at least one coil and/or the at least one electric connection cable of afore-mentioned embodiment is reduced in the form of a reduced psychoacoustic loudness and/or a reduced peak sound pressure level and/or a reduced sound energy and/or a reduced psychoacoustic roughness and/or a reduced psychoacoustic sharpness.

In a preferred embodiment, the at least one coil and/or the at least one electric connection cable of one of the afore-mentioned embodiments includes at least one viscoelastic material layer and/or at least one elastic material layer.

In a preferred embodiment, at least one conductor of the at least one coil of one of the afore-mentioned embodiments and/or of the at least one electric connection cable of one of the afore-mentioned embodiments comprises at least two different metals, each of which can be an alloy, wherein the at least two metals are mechanically tightly connected to each other in at least one interface, and wherein at least one of the at least two metals has at least twice the electric conductivity and at maximum half of the Young's modulus of at least one of the at least two metals.

In a preferred embodiment, the at least two metals of one of the afore-mentioned embodiments are arranged such in the cross section of the at least one conductor that the metal of the at least two metals with the highest electric conductivity is located in areas of high current density and wherein at most one third of the electric current of the short and strong current pulse, which is not homogeneously distributed across the cross section of the at least one conductor due to electric high-frequency effects, flows through that metal of the at least two metals that has the lowest electric conductivity.

In a preferred embodiment, the Young's modulus of the at least one elastic material layer of one of the afore-mentioned embodiments is smaller than an eighth of the Young's modulus of the mechanically stiff polymer and/or a mechanically stiff synthetic material and/or a mechanically stiff composite material and/or a mechanically stiff ceramic material and/or a mechanically stiff glass.

In a preferred embodiment, the product of viscosity and Young's modulus of the at least one viscoelastic material layer of one of the afore-mentioned embodiments is higher than 10 billion pascal-squared seconds.

In a preferred embodiment, at least one viscoelastic material layer covers at least one third of the surface of the stiff unit of one of the afore-mentioned embodiments and is mechanically tightly connected to the surface, wherein the viscoelastic material layer can be covered by further material layers, and wherein the stiff unit is formed by the at least one electric conductor embedded into a mechanically stiff polymer and/or a mechanically stiff synthetic material and/or a mechanically stiff composite material and/or a mechanically stiff ceramic material and/or a mechanically stiff glass.

In a preferred embodiment, at least one elastic material layer covers at least one third of the surface of the stiff unit of one of the afore-mentioned embodiments and/or of a viscoelastic material layer that partly covers said stiff unit of the afore-mentioned embodiments, wherein the stiff unit is formed by the at least one electric conductor embedded into a mechanically stiff polymer and/or a mechanically stiff synthetic material and/or a mechanically stiff composite material and/or a mechanically stiff ceramic material and/or a mechanically stiff glass.

In a preferred embodiment, an elastic material layer covers at least a portion of that surface of the coil that has a mechanical contact to the body tissue of one of the afore-mentioned embodiments.

In a preferred embodiment, the at least one elastic material layer of one of the afore-mentioned embodiments consists of a material that is member of the class of soft matter;
or consists of a gas;
or consists of a vacuum;
or consists of a compound of a solid material and/or a material of soft matter and a gas;
or consists of a solid material and/or a material of soft matter and a vacuum;
or consists of a polymer foam;
or consists of a liquid;
or consists of a composite of a solid material and/or a material of soft matter and a liquid;
or comprises a spring mechanisms made from a solid material in a gas and/or a vacuum.

In a preferred embodiment, the material of the at least one elastic material layer of one of the afore-mentioned embodiments is an elastomer and/or a molten polymer and/or a gel and/or a colloidal suspension.

In a preferred embodiment, less than a quarter of the energy of the electric current pulse of one of the afore-mentioned embodiments is in the frequency range from 500 Hz to 8000 Hz.

In a preferred embodiment, the basic frequency and/or the dominant frequency of the electric current pulse of one of the afore-mentioned embodiments is higher than the human hearing limit of 18 kHz.

In a preferred embodiment, less than a quarter of the energy of the electric current pulse of one of the afore-mentioned embodiments is in the frequency range of 500 Hz to 18 kHz.

In a preferred embodiment, the electric current pulse of one of the afore-mentioned embodiments comprises exactly one zero crossing at which the current changes from one polarity to the other, and wherein the total duration of the current pulse is shorter than 75 microseconds.

In a preferred embodiment, the electric current pulse of one of the afore-mentioned embodiments comprises a sinusoidal oscillation whose amplitude envelope rises from a value lower than one fifth of the maximum in less than 500 microseconds to a maximum and subsequently falls below one fifth of the maximum within less than 500 microseconds, wherein the frequency of the sinusoidal oscillation may change during the current pulse in a continuous way.

In a preferred embodiment, the electric current pulse of one of the afore-mentioned embodiments is generated by a pulse source that contains a multilevel converter with at least three capacitors and which generates a current pulse by dynamic electrical combination of the at least three capacitors, wherein the electric pulse source is able to generate current pulses with different amplitudes and shape, wherein the amplitude and shape can be modified independent from each other between the generation of two subsequent current pulses.

In a preferred embodiment, the electric current pulse of one of the afore-mentioned embodiments is generated by a pulse source that contains a multilevel converter with at least three capacitors and which generates a current pulse by dynamic electrical combination of the at least three capacitors, wherein the electric pulse source is able to generate current pulses with different amplitudes and shape, wherein the amplitude and shape can be modified independent from each other between the generation of two subsequent current pulses.

In a preferred embodiment, the electric current pulse of one of the afore-mentioned embodiments is generated by a pulse source that contains a multilevel converter with at least three capacitors and which generates a current pulse by dynamic electrical combination of the at least three capacitors, wherein the electric pulse source is able to generate current pulses with different amplitudes and shape, wherein the amplitude and shape can be modified independent from each other between the generation of two subsequent current pulses.

In a preferred embodiment, the electric current pulse of one of the afore-mentioned embodiments is generated by a pulse source that contains at least three capacitors and which generates a current pulse by dynamic electrical combination of the at least three capacitors, wherein the electric pulse source is able to generate current pulses with different amplitudes and shape, wherein the amplitude and shape can be modified independent from each other between the generation of two subsequent current pulses.

In a preferred embodiment, the electric current pulse of one of the afore-mentioned embodiments is generated by a pulse source that contains at least one capacitor (1701, 1901, 1902, 2001, 2002) and at least one electronic switch (1702, 1903, 1904) that can be turned off (e.g., an IGBT).

In a preferred embodiment, the electric current pulse of one of the afore-mentioned embodiments is generated by a pulse source that contains at least one capacitor (1901, 1902, 2001, 2002) and at least two electronic switches (1903, 1904, 2003, 2004) that can be turned off (e.g., an IGBT). and that are connected electrically in series, wherein the electric connection between the at least two electronic switches is electrically connected via at least a third electrical connection either immediately or indirectly via at least one electrical element with at least one terminal of the coil (1907, 2007).

The invention claimed is:

1. A device for generating a current pulse with a total duration of less than two milliseconds in at least one coil such that the at least one coil generates magnetic field pulses, which are configured to induce electrical currents in body tissue and evoke action potentials in neurons or myocytes, wherein the at least one coil is designed such that the generated magnetic field pulses can permeate the body tissue; and
wherein the device comprises at least one capacitor for storing energy for the magnetic field pulses;
wherein the device is designed such that at least one electric conductor of the at least one coil or of at least one electric connection cable that connects to the at least one coil is embedded in one or more of the following acoustic dampening materials: (i) a mechanically stiff polymer, (ii) a mechanically stiff synthetic material, (iii) a mechanically stiff composite material, (iv) a mechanically stiff ceramic material, or (v) a mechanically stiff glass, the one or more acoustic dampening materials forming a stiff unit, the stiff unit configured to reduce sound emitted by the at least one coil or the at least one electric connection cable as a result of the current pulse;
wherein a basic frequency or a dominant frequency of the current pulse is higher than 18 kHz; and
wherein less than a quarter of an energy of the electric current pulse is in the frequency range from 500 Hz to 8000 Hz.

2. A device according to claim 1 wherein the one or more acoustic dampening materials are configured to reduce one or more of a psychoacoustic loudness, a peak sound pressure level, a sound energy, a psychoacoustic roughness, or a psychoacoustic sharpness.

3. A device according to claim 1 wherein the at least one coil or the at least one electric connection cable includes at least one viscoelastic material layer or at least one elastic material layer.

4. A device according to claim 1 wherein at least one electric conductor of the at least one coil or of the at least one electric connection cable comprises at least two different metals, wherein the at least two metals are mechanically tightly connected to each other in at least one interface, and wherein at least one of the at least two metals has at least twice the electric conductivity and at maximum half of the Young's modulus of at least one of the other at least two metals.

5. A device according to claim 4 wherein the at least two metals are arranged such that in the cross section of the at least one conductor that the metal of the at least two metals with a highest electric conductivity of the least two metals is located in areas of high current density and wherein at most one third of the electric current of the current pulse flows through the metal of the at least two metals that has a lowest electric conductivity of the at least two metals.

6. A device according to claim 3 wherein the Young's modulus of the at least one elastic material layer is smaller than an eighth of the Young's modulus of the one or more acoustic dampening materials; or wherein a product of viscosity and Young's modulus of the at least one viscoelastic material layer is higher than 10 billion pascal-squared seconds.

7. A device according to claim 1, wherein at least one viscoelastic material layer covers at least one third of a surface of the stiff unit and is mechanically tightly connected to the surface.

8. A device according to claim 1, wherein at least one elastic material layer covers at least one third of a surface of the stiff unit or of a viscoelastic material layer that partly covers said stiff unit.

9. A device according to claim 8 wherein the material of the at least one elastic material layer is an elastomer, a molten polymer, a gel, or a colloidal suspension.

10. A device according to claim 1 wherein the current pulse comprises exactly one zero crossing at which the current changes from one polarity to the other, and wherein the total duration of the current pulse is shorter than 75 microseconds.

11. A device according to claim 1 wherein the current pulse comprises a sinusoidal oscillation whose amplitude envelope rises from a value lower than one fifth of a maximum amplitude in less than 500 microseconds to the maximum amplitude and subsequently falls below one fifth of the maximum amplitude within less than 500 microseconds, wherein a frequency of the sinusoidal oscillation changes during the current pulse in a continuous way.

12. A device according to claim 1 wherein the current pulse is generated by an electric pulse source that contains a multilevel converter with at least three capacitors and which generates the current pulse by dynamic electrical combination of the at least three capacitors, wherein the electric pulse source is able to generate current pulses with different amplitudes and shapes, wherein an amplitude and a shape can be modified independent from each other between the generation of two subsequent current pulses.

13. A device according to claim 1, wherein the current pulse is generated by a pulse source that contains at least one capacitor and at least one electronic switch that can be turned off.

14. A device according to claim 1, wherein the current pulse is generated by a pulse source that contains at least one capacitor and at least two electronic switches that can be turned off and that are connected electrically in series, wherein the electric connection between the at least two electronic switches is electrically connected via at least a third electrical connection either immediately or indirectly via at least one electrical element with at least one terminal of the at least one coil.

15. A device for generating a current pulse with a total duration of less than two milliseconds in at least one coil such that the at least one coil generates magnetic field pulses, which are configured to induce electrical currents in body tissue and evoke action potentials in neurons or myocytes, wherein the at least one coil is designed such that the generated magnetic field pulses can permeate the body tissue; and
wherein the device comprises at least one capacitor for storing energy for the magnetic field pulses;
wherein the device is designed such that at least one electric conductor of the at least one coil or of at least one electric connection cable that connects to the at least one coil is embedded in one or more of the following acoustic dampening materials: (i) a mechanically stiff polymer, (ii) a mechanically stiff synthetic material, (iii) a mechanically stiff composite material, (iv) a mechanically stiff ceramic material, or (v) a mechanically stiff glass, the one or more acoustic dampening materials forming a stiff unit, the stiff unit configured to reduce sound emitted by the at least one coil or the at least one electric connection cable as a result of the current pulse; and wherein a basic frequency or a dominant frequency of the current pulse is higher than 18 kHz.

* * * * *